United States Patent
Laberge et al.

(10) Patent No.: US 12,285,427 B2
(45) Date of Patent: *Apr. 29, 2025

(54) TREATMENT OF A SENESCENCE-ASSOCIATED OCULAR DISEASE OR DISORDER USING A Bcl-xL SELECTIVE INHIBITOR

(71) Applicants: Buck Institute for Research on Aging, Novato, CA (US); Mayo Foundation for Medical Education and Research, Rochester, MN (US); Unity Biotechnology, Inc., South San Francisco, CA (US)

(72) Inventors: Remi-Martin Laberge, South San Francisco, CA (US); Judith Campisi, Berkeley, CA (US); Marco Demaria, San Francisco, CA (US); Bennett G. Childs, Rochester, MN (US); Jan M. A. Van Deursen, Rochester, MN (US); Nathaniel David, South San Francisco, CA (US); Alain Philippe Vasserot, South San Francisco, CA (US)

(73) Assignees: Unity Biotechnology, Inc., South San Francisco, CA (US); Mayo Foundation for Medical Education and Research, Rochester, MN (US); Buck Institute for Research on Aging, Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/215,731

(22) Filed: Aug. 7, 2023

(65) Prior Publication Data

US 2024/0115563 A1 Apr. 11, 2024

Related U.S. Application Data

(63) Continuation of application No. 17/548,004, filed on Dec. 10, 2021, which is a continuation of application
(Continued)

(51) Int. Cl.
| | |
|---|---|
| A61K 31/496 | (2006.01) |
| A61K 9/00 | (2006.01) |
| A61K 31/404 | (2006.01) |
| A61K 31/4178 | (2006.01) |
| A61K 31/428 | (2006.01) |
| A61K 31/4375 | (2006.01) |
| A61K 31/495 | (2006.01) |
| A61K 31/5377 | (2006.01) |
| A61K 31/728 | (2006.01) |
| A61K 45/06 | (2006.01) |
| A61K 47/36 | (2006.01) |

(Continued)

(52) U.S. Cl.
CPC .......... *A61K 31/496* (2013.01); *A61K 9/0048* (2013.01); *A61K 9/0073* (2013.01); *A61K 31/404* (2013.01); *A61K 31/4178* (2013.01); *A61K 31/428* (2013.01); *A61K 31/4375* (2013.01); *A61K 31/495* (2013.01); *A61K 31/5377* (2013.01); *A61K 31/728* (2013.01); *A61K 45/06* (2013.01); *A61K 47/36* (2013.01); *A61P 9/10* (2018.01); *A61P 11/00* (2018.01); *A61P 25/16* (2018.01); *A61P 27/02* (2018.01); *C12N 5/0081* (2013.01); *A61P 25/28* (2018.01); *C12N 2501/999* (2013.01); *C12N 2503/02* (2013.01); *C12Q 1/485* (2013.01)

(58) Field of Classification Search
CPC ................................ A61P 27/02–12
See application file for complete search history.

(56) References Cited

U.S. PATENT DOCUMENTS

| | | |
|---|---|---|
| 5,856,171 A | 1/1999 | Korsmeyer |
| 6,617,346 B1 | 9/2003 | Kong et al. |

(Continued)

FOREIGN PATENT DOCUMENTS

| | | |
|---|---|---|
| EP | 3139942 | 3/2017 |
| KR | 20120118596 A | 10/2012 |

(Continued)

OTHER PUBLICATIONS

Anderson et al., "Why is Osteoarthritis an Age-Related Disease?", Best Pract Res Clin Rheumatol., vol. 24, No. 1, Feb. 2010, 15 pages.
Arya et al., "Nutlin-3, the Small-Molecule Inhibitor of MDM2, Promotes Senescence and Radiosensitises Laryngeal Carcinoma Cells Harbouring Wild-Type p53", Br J Cancer, vol. 103, No. 2, Jul. 13, 2010, pp. 186-195, doi: 10.1038/sj.bjc.6605739, Epub Jun. 29, 2010.
Axanova et al., "1,25-Dihydroxyvitamin D3 and PI3K/AKT Inhibitors Synergistically Inhibit Growth and Induce Senescence in Prostate Cancer Cells", Prostate, vol. 70, No. 15, Nov. 1, 2010, pp. 1658-1671.

(Continued)

*Primary Examiner* — Theodore R. Howell
(74) *Attorney, Agent, or Firm* — Rudy J. Ng; Melissa Nakamoto; Bozicevic, Field & Francis LLP

(57) ABSTRACT

This invention establishes a new paradigm for treatment of Parkinson's disease (PD) by eliminating senescent cells that reside in or around the site of the disease pathophysiology. Exposure of test subjects to the herbicide paraquat (PQ) increases the risk for developing Parkinson's disease. The data in this disclosure show that PQ induces a senescence arrest and SASP in astrocytes, in culture and in vivo in mice, and senescent cell markers were present in astrocytes in midbrain tissue from PD patients. In a transgenic mouse model, senescent cell ablation protected against PQ-induced PD-like neuropathology. Removal of senescent cells from affected sites using small molecule agents that specifically target senescent cells can help prevent or ameliorate signs and symptoms of the disease.

4 Claims, 10 Drawing Sheets

Related U.S. Application Data

Figure 1A:
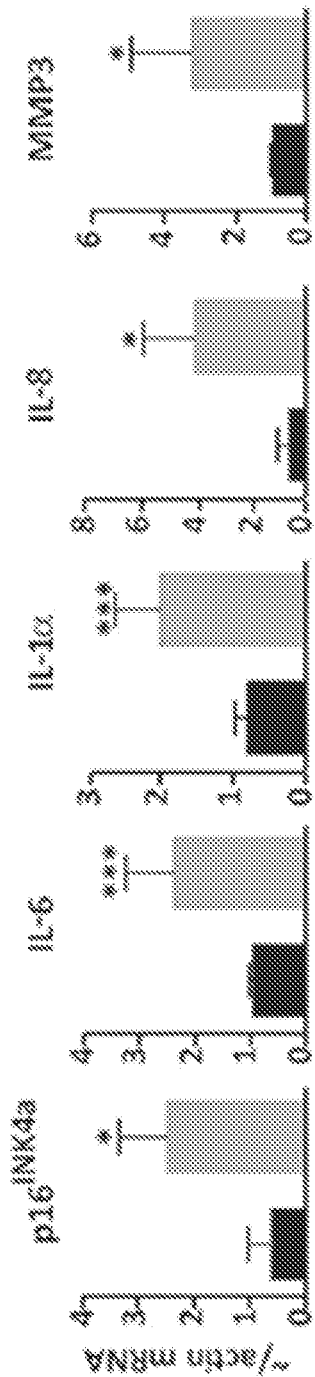

No. 16/403,389, filed on May 3, 2019, now abandoned, which is a continuation-in-part of application No. 15/950,965, filed on Apr. 11, 2018, now Pat. No. 10,413,542, which is a continuation of application No. 15/114,762, filed as application No. PCT/US2015/013387 on Jan. 28, 2015, now Pat. No. 9,993,472.

(60) Provisional application No. 62/061,627, filed on Oct. 8, 2014, provisional application No. 62/061,629, filed on Oct. 8, 2014, provisional application No. 62/057,828, filed on Sep. 30, 2014, provisional application No. 62/057,825, filed on Sep. 30, 2014, provisional application No. 62/057,820, filed on Sep. 30, 2014, provisional application No. 62/044,664, filed on Sep. 2, 2014, provisional application No. 62/042,708, filed on Aug. 27, 2014, provisional application No. 62/002,709, filed on May 23, 2014, provisional application No. 61/979,911, filed on Apr. 15, 2014, provisional application No. 61/932,704, filed on Jan. 28, 2014, provisional application No. 61/932,711, filed on Jan. 28, 2014.

(51) Int. Cl.
| | |
|---|---|
| *A61P 9/10* | (2006.01) |
| *A61P 11/00* | (2006.01) |
| *A61P 25/16* | (2006.01) |
| *A61P 27/02* | (2006.01) |
| *C12N 5/00* | (2006.01) |
| *A61P 25/28* | (2006.01) |
| *C12Q 1/48* | (2006.01) |

(56) References Cited

U.S. PATENT DOCUMENTS

| | | |
|---|---|---|
| 6,734,302 B2 | 5/2004 | Kong et al. |
| 7,482,134 B2 | 1/2009 | Jang et al. |
| 7,705,007 B2 | 4/2010 | Fotouhi et al. |
| 7,767,684 B2 | 8/2010 | Bruncko et al. |
| 7,842,681 B2 | 11/2010 | Elmore et al. |
| 7,851,626 B2 | 12/2010 | Ding et al. |
| 7,893,278 B2 | 2/2011 | Haley et al. |
| 8,114,893 B2 | 2/2012 | Baell et al. |
| 8,168,645 B2 | 5/2012 | Baell et al. |
| 8,168,784 B2 | 5/2012 | Franczyk, II et al. |
| 8,343,967 B2 | 1/2013 | Ding et al. |
| 8,426,422 B2 | 4/2013 | Hexamer et al. |
| 8,563,735 B2 | 10/2013 | Bruncko et al. |
| 8,586,754 B2 | 11/2013 | Bruncko et al. |
| 8,691,184 B2 | 4/2014 | Wang et al. |
| 9,018,381 B2 | 4/2015 | Diebold et al. |
| 9,248,140 B2 | 2/2016 | Diebold et al. |
| 9,266,860 B2 | 2/2016 | Guy et al. |
| 9,360,471 B2 | 6/2016 | Qi |
| 9,527,847 B2 | 12/2016 | Palombella et al. |
| 9,630,990 B2 | 4/2017 | Shetty et al. |
| 9,849,128 B2 | 12/2017 | Laberge et al. |
| 9,855,266 B2 | 1/2018 | Laberge et al. |
| 9,980,962 B2 | 5/2018 | Laberge et al. |
| 10,010,546 B2 * | 7/2018 | Laberge .................. A61P 27/02 |
| 10,213,426 B2 | 2/2019 | Laberge et al. |
| 10,328,073 B2 * | 6/2019 | Laberge ............... A61K 31/495 |
| 10,478,432 B2 * | 11/2019 | Laberge .................. A61P 9/10 |
| 11,351,167 B2 | 6/2022 | Laberge et al. |
| 2002/0054915 A1 | 5/2002 | Goldenheim et al. |
| 2002/0197602 A1 | 12/2002 | Burmer et al. |
| 2003/0086916 A1 | 5/2003 | Goligorsky et al. |
| 2004/0242545 A1 | 12/2004 | Otsuka et al. |
| 2005/0019865 A1 | 1/2005 | Kihm et al. |
| 2005/0181076 A1 | 8/2005 | Ziegler |
| 2005/0282803 A1 | 12/2005 | Haley et al. |
| 2006/0122150 A1 | 6/2006 | Argentieri et al. |
| 2007/0129416 A1 | 6/2007 | Ding et al. |
| 2008/0221132 A1 | 9/2008 | Cai et al. |
| 2008/0234362 A1 | 9/2008 | Chandler |
| 2009/0105319 A1 | 4/2009 | Pellecchia et al. |
| 2010/0016218 A1 | 1/2010 | Lichter et al. |
| 2010/0087436 A1 | 4/2010 | Bardwell et al. |
| 2010/0152183 A1 | 6/2010 | Bruncko et al. |
| 2010/0227838 A1 | 9/2010 | Shah et al. |
| 2010/0292200 A1 | 11/2010 | Kile et al. |
| 2010/0310504 A1 | 12/2010 | Lowe et al. |
| 2011/0028437 A1 | 2/2011 | Robbins et al. |
| 2011/0071151 A1 | 3/2011 | Zhang et al. |
| 2011/0212909 A1 | 9/2011 | Wen et al. |
| 2011/0218206 A1 | 9/2011 | Chan |
| 2012/0028925 A1 | 2/2012 | Tao et al. |
| 2012/0035134 A1 | 2/2012 | Diebold et al. |
| 2012/0046333 A1 | 2/2012 | Hardie et al. |
| 2012/0108590 A1 | 5/2012 | Birtalan et al. |
| 2012/0115880 A1 | 5/2012 | Dyer et al. |
| 2012/0129853 A1 | 5/2012 | Elmore et al. |
| 2012/0156134 A1 | 6/2012 | Squires |
| 2012/0172285 A1 | 7/2012 | Walensky et al. |
| 2012/0183534 A1 | 7/2012 | Gruber |
| 2012/0276093 A1 | 11/2012 | Ballinari et al. |
| 2012/0277210 A1 | 11/2012 | Catron et al. |
| 2012/0283269 A1 | 11/2012 | Blagosklonny et al. |
| 2013/0096121 A1 | 4/2013 | Wang et al. |
| 2013/0149314 A1 | 6/2013 | Bullerdiek et al. |
| 2013/0225594 A1 | 8/2013 | Craighead et al. |
| 2013/0225603 A1 | 8/2013 | Chavala et al. |
| 2013/0267534 A1 | 10/2013 | Bruncko et al. |
| 2013/0287763 A1 | 10/2013 | Sathyanarayanan et al. |
| 2013/0302283 A1 | 11/2013 | Kihm |
| 2013/0317043 A1 | 11/2013 | Wagner et al. |
| 2014/0005190 A1 | 1/2014 | Baell et al. |
| 2014/0017341 A1 | 1/2014 | Gourlaouen |
| 2014/0018302 A1 | 1/2014 | Walensky et al. |
| 2014/0073640 A1 | 3/2014 | Judd et al. |
| 2014/0134163 A1 | 5/2014 | Errico et al. |
| 2014/0220111 A1 | 8/2014 | Hayes et al. |
| 2014/0242545 A1 | 8/2014 | Brun |
| 2014/0256721 A1 | 9/2014 | Hamblin et al. |
| 2014/0272947 A1 | 9/2014 | Zhang et al. |
| 2014/0275082 A1 | 9/2014 | Tao et al. |
| 2014/0328893 A1 | 11/2014 | Adnot |
| 2015/0051215 A1 | 2/2015 | Wooster et al. |
| 2015/0126573 A1 | 5/2015 | Boczkowski et al. |
| 2015/0140036 A1 | 5/2015 | Mannick et al. |
| 2015/0231136 A1 | 8/2015 | Chavala et al. |
| 2016/0000744 A1 | 1/2016 | Day et al. |
| 2016/0022720 A1 | 1/2016 | Jordan |
| 2016/0122758 A1 | 5/2016 | Krizhanovsky et al. |
| 2017/0056421 A1 * | 3/2017 | Zhou ................... A61K 31/635 |
| 2017/0119789 A1 | 5/2017 | Campisi et al. |
| 2017/0196858 A1 | 7/2017 | Laberge et al. |
| 2017/0198253 A1 | 7/2017 | Laberge et al. |
| 2017/0348307 A1 | 12/2017 | Laberge et al. |
| 2018/0104222 A1 | 4/2018 | Childs et al. |

FOREIGN PATENT DOCUMENTS

| | | |
|---|---|---|
| KR | 20130139512 A | 12/2013 |
| WO | WO2003028443 A1 | 4/2003 |
| WO | WO2003051359 A1 | 6/2003 |
| WO | WO2006018632 A2 | 2/2006 |
| WO | WO2006039704 A2 | 4/2006 |
| WO | WO2008113131 A1 | 9/2008 |
| WO | WO2008125487 A1 | 10/2008 |
| WO | WO2009039553 A1 | 4/2009 |
| WO | WO2009105234 A2 | 8/2009 |
| WO | WO2010080478 A1 | 7/2010 |
| WO | WO2010148447 A1 | 12/2010 |
| WO | WO2011068560 A1 | 6/2011 |
| WO | WO2011083150 | 7/2011 |
| WO | WO2014186878 A1 | 11/2014 |
| WO | WO2015051252 A1 | 4/2015 |
| WO | WO2015066442 A1 | 5/2015 |

(56) References Cited

FOREIGN PATENT DOCUMENTS

| WO | WO2015116735 A1 | 8/2015 |
|---|---|---|
| WO | WO2015116740 A1 | 8/2015 |
| WO | WO2015181526 A1 | 12/2015 |

OTHER PUBLICATIONS

Bajwa et al, "Inhibitors of the Anti-Apoptotic Bcl-2 Proteins: A Patent Review", Expert Opin Ther Pat., vol. 22, No. 1, Jan. 2012, pp. 37-55, doi: 10.1517/13543776.2012.644274, Epub Dec. 23, 2011.
Baker et al., "Clearance of p16Ink4a-Positive Senescent Cells Delays Ageing-Associated Disorders", Nature, vol. 479, No. 7372, 2011, pp. 232-236.
Barak et al., "Mdm2 Expression is Induced by Wild Type p53 Activity", EMBO J., vol. 12, No. 2, Feb. 1993, pp. 461-468.
Berenbaum (2013) "Osteoarthritis as an inflammatory disease (osteoarthritis is not osteoarthrosis!)", Osteoarthritis and Cartilage 21:16-21.
Brenkman et al., "Mdm2 Induces Mono-Ubiquitination of FOX04", PLoS One, vol. 3, No. 7, Jul. 30, 2008, e2819. doi: 10.1371/journal. pone.0002819.
Campisi et al., "Cell Senescence: Role in Aging and Age-Related Diseases", Interdiscip Top Gerontol., vol. 39, 2014, pp. 45-61, doi: 10.1159/000358899, Epub May 13, 2014.
Campisi, J., "Cellular Senescence as a Tumor-Suppressor Mechanism", Trends Cell Biol., vol. 11, No. 11, Nov. 2001, pp. S27-S31.
Campisi, J., "Cellular Senescence: Putting the Paradoxes in Perspective", Curr Opin Genet Dev., vol. 21, No. 1, Feb. 2011, pp. 107-112, doi: 10.1016/j.gde.2010.10.005, Epub Nov. 17, 2010.
Campisi, J., "Senescent Cells, Tumor Suppression, and Organismal Aging: Good Citizens, Bad Neighbors", Cell, vol. 120, No. 4, Feb. 25, 2005, pp. 513-522.
Caruso et al., "Apoptotic-Like Tumor Cells and Apoptotic Neutrophils in Mitochondrion-Rich Gastric Adenocarcinomas: A Comparative Study with Light and Electron Microscopy Between these Two Forms of Cell Death", Rare Tumors, vol. 5, No. 2, Jun. 7, 2013, pp. 68-71, doi: 10.4081/rt.2013.e18, Print Apr. 15, 2013.
Chang et al., "Clearance of Senescent Cells by ABT263 Rejuvenates Aged Hematopoietic Stem Cells in Mice", Nat Med., vol. 22, Dec. 14, 2015, pp. 78-83, doi: 10.1038/nm.4010.
Chappell et al., "Ras/Raf/MEK/ERK and PI3K/PTEN/Akt/mTOR Inhibitors: Rationale and Importance to Inhibiting these Pathways in Human Health", Oncotarget., vol. 2, No. 3, Mar. 2011, pp. 135-164.
Co-pending U.S. Application: David et al., "Treatment of Joint Pain", U.S. Appl. No. 15/481,129, filed Apr. 6, 2017.
Co-pending U.S. Application: Remi-Martin Laberge et al., "Treatment of Ophthalmic Conditions by Selectively Removing Senescent Cells from the Eye", U.S. Appl. No. 15/827,539, filed Nov. 30, 2017.
Co-Pending U.S. Application: Laberge et al., "Treating Pulmonary Conditions by Selectively Removing Senescent Cells from the Lung using an Intermittent Dosing Regimen", U.S. Appl. No. 15/955,542, filed Apr. 17, 2018.
Co-Pending U.S. Application: Laberge et al. "Removing Senescent Cells from a Mixed Cell Population or Tissue using a Phosphoinositide 3-Kinase (Pi3k) Inhibitor", U.S. Appl. No. 15/981,696, filed May 16, 2018.
Co-Pending U.S. Application: Laberge et al., "Use of Sulfonamide Inhibitors of Bcl-2 and Bcl-XI To Treat Ophthalmic Disease By Selectively Removing Senescent Cells" U.S. Appl. No. 16/054,667, filed Aug. 3, 2018, pp. 1-248.
Coppe et al., "A Human-Like Senescence-Associated Secretory Phenotype is Conserved in Mouse Cells Dependent on Physiological Oxygen", PLoS One, vol. 5, 2010, e9188.
Coppe et al., "Senescence-Associated Secretory Phenotypes Reveal Cell-Nonautonomous Functions of Oncogenic RAS and the p53 Tumor Suppressor", PLoS Biol., vol. 6, No. 12, Dec. 2, 2008, pp. 2853-2868, doi: 10.1371/journal.pbio.0060301.

Dienstmann et al., "Picking the Point of Inhibition: A Comparative Review of PI3K/AKT/mTOR Pathway Inhibitors", Mol Cancer Ther., vol. 13, No. 5, May 2014, pp. 1021-1031, Epub Apr. 18, 2014.
Doroshevskaya et al., "Apoptosis Regulator Proteins: Basis for the Development of Innovation Strategies for the Treatment of Rheumatoid Arthritis in Patients of Different Age". Bulletin of Experimental Biology and Medicine, vol. 156, No. 3, Jan. 2014, pp. 377-380.
Efeyan et al., "Induction of p53-dependent Senescence by the MDM2 Antagonist Nutlin-3a in Mouse Cells of Fibroblast Origin", Cancer Res., vol. 67, No. 15, Aug. 1, 2007, pp. 7350-7357.
Laberge et al., "Methods and Compositions for Killing Senescent Cells and for Treating Senescence-Associated Diseases and Disorders", Extended European Search Report and Search Opinion received for European Application No. 15743068.7, dated Aug. 28, 2017.
Laberge et al., "Unit Dose of a Cis-Imidazoline for Treating an Osteoarthritic Joint by Removing Senescent Cells", First Action Interview Pilot Program Pre-Interview Communication received for U.S. Appl. No. 15/455,575, dated May 16, 2017.
Freund et al., p38MAPK is a Novel DNA Damage Response-Independent Regulator of the Senescence-Associated Secretory Phenotype, EMBO J., vol. 30, No. 8, Apr. 20, 2011, pp. 1536-1548, doi: 10.1038/emboj.2011.69, Epub Mar. 11, 2011.
Gagarina et al., "SirT1 Enhances Survival of Human Osteoarthritic Chondrocytes by Repressing Protein Tyrosine Phosphatase 18 and Activating the Insulin-Like Growth Factor Receptor Pathway", Arthritis Rheum., vol. 62, No. 5, May 2010, pp. 1383-1392.
Gannon et al., "Mdm2-p53 Signaling Regulates Epidermal Stem Cell Senescence and Premature Aging Phenotypes in Mouse Skin". Developmental Biology, vol. 353, 2011, pp. 1-9.
Golstein et al., "Cell Death by Necrosis: Towards a Molecular Definition", Trends in Biochemical Sciences, vol. 32, No. 1, Jan. 2007, pp. 37-43.
Guan et al. "Imidazoline Derivatives: A Patent Review (2006-present)", Expert Opin Ther Pat., vol. 22, No. 11, Nov. 2012, pp. 1353-1365, doi: 10.1517/13543776.2012.727397, Epub Sep. 24, 2012.
Hashimoto et al. "Role of p53 in Human Chondrocyte Apoptosis in Response to Shear Strain", Arthritis Rheum., vol. 60, No. 8, Aug. 2009, pp. 2340-2349.
Haupt et al., "Mdm2 Promotes the Rapid Degradation of p53", Nature, vol. 387, No. 6630, May 15, 1997, pp. 296-299.
Holford et al., "Phannacokinetics and Phannacodynamics: Dose Selection & the Time Course of Drug Action", In: Katzung B.G., ed. Basic & Clinical Pharmacology (7th ed.), Appleton & Lange, Stamford, CT, 1998, pp. 34-49.
Honda et al., "Oncoprotein MDM2 is a Ubiquitin Ligase E3 for Tumor Suppressor p53", FEBS Lett., vol. 420, No. 1, Dec. 22, 1997, pp. 25-27.
Huang et al. "Reduced Transcriptional Activity in the p53 Pathway of Senescent Cells Revealed by the MDM2 Antagonist Nutlin-3", Aging (Albany NY), vol. 1, No. 10, Oct. 2009, pp. 845-854, doi: 10.18632/aging.100091, Epub Sep. 25, 2009.
Ianitti et al., "Intra-Articular Injections for the Treatment of Osteoarthritis: Focus on the Clinical Use of Hyaluronic Acid", Drugs R D., vol. 11, No. 1, 2011, pp. 13-27.
Kirkland et al. "Methods and Combinations for Killing Senescent Cells and for Treating Senescence-Associated Diseases and Disorders", International Preliminary Report on Patentability received for PCT Patent Application No. PCT/US2015/013376, dated Aug. 2, 2016.
Laberge et al., "Methods and Compositions for Killing Senescent Cells and for Treating Senescence-Associated Diseases and Disorders", International Preliminary Report on Patentability received for PCT Patent Application No. PCT/US2015/013387, dated Aug. 2, 2016.
Jakubsick et. al., "Human Pulmonary Fibroblasts Exhibit Altered Interleukin-4 and Interleukin-13 Receptor Subunit Expression in Idiopathic Interstitial Pneumonia", Am J Pathol., vol. 164, No. 6, Jun. 2004, pp. 1989-2001.
Jeon et al., "Local Clearance of Senescent Cells Attenuates the Development of Post-Traumatic Osteoarthritis and Creates a Pro-

(56) References Cited

OTHER PUBLICATIONS

Regenerative Environment", Nat Med., vol. 23, No. 6, Jun. 2017, pp. 775-781, doi: 10.1038/nm.4324, Epub Apr. 24, 2017.
Juven et al., "Wild Type p53 can Mediate Sequence-Specific Transactivation of an Internal Promoter within the Mdm2 Gene", Oncogene, vol. 8, No. 12, Dec. 1993, pp. 3411-3416.
Kegel, Magdalena, "Cancer Drug Candidate to be Tested on Lung Fibrosis in Phase 1 Clinical Trial", Pulmonary Fibrosis News, May 2, 2016, pp. 1-2.
Kerr et al., "Apoptosis: A Basic Biological Phenomenon with Wide-Ranging Implications in Tissue Kinetics", Br J Cancer, vol. 26, No. 4, Aug. 1972, pp. 239-257.
Kroemer et al., "Classification of Cell Death: Recommendations of the Nomenclature Committee on Cell Death 2009", Cell Death Differ., vol. 16, No. 1, Jan. 2009, pp. 3-11.
Kubbutat et al., "Regulation of p53 Stability by Mdm2", Nature, vol. 387, No. 6630, May 15, 1997, pp. 299-303.
Laberge et al., "Glucocorticoids Suppress Selected Components of the Senescence-Associated Secretory Phenotype", Aging Cell, vol. 11, No. 4, 2012, pp. 569-578.
Laberge et al., "Mitochondrial DNA Damage Induces Apoptosis in Senescent Cells", Cell Death Dis., vol. 4, Jul. 18, 2013, e727, doi: 10.1038/cddis.2013.199.
Lahav, Galit, "Oscillations by the p53-Mdm2 Feedback Loop", Adv Exp Med Biol., vol. 641, 2008, pp. 28-38.
Le Cras et al., "Inhibition of PI3K by PX-866 Prevents Transforming Growth Factor-α-Induced Pulmonary Fibrosis", Am J Pathol., vol. 176, No. 2, Feb. 2010, pp. 679-686, Epub Dec. 30, 2009.
Leist et al., "Four Deaths and A Funeral: From Caspases to Alternative Mechanisms", Nat Rev Mol Cell Biol., vol. 2, No. 8, Aug. 2001, pp. 589-598.
Lessene et al., "Structure-Guided Design of a Selective BCL-X(L) Inhibitor", Nat Chem Biol., vol. 9, No. 6, Jun. 2013, pp. 390-397.
Liu et al., "The PI3K-Akt Pathway Inhibits Senescence and Promotes Self-Renewal of Human Skin-derived Precursors in Vitro", Aging Cell, vol. 10, No. 4, Aug. 2011, pp. 661-674, Epub May 3, 2011.
Loeser, Richard F., "Aging and Osteoarthritis: The Role of Chondrocyte Senescence and Aging Changes in the Cartilage Matrix", Osteoarthritis Cartilage, vol. 17, No. 8, Aug. 2009, pp. 971-979, doi: 10.1016/j.joca.2009.03.002, Epub Mar. 12, 2009.
Manfredi, James, "The Mdm2-p53 Relationship Evolves: Mdm2 Swings Both Ways as an Oncogene and a Tumor Suppressor", Genes Dev., vol. 24, No. 15, Aug. 1, 2010, pp. 1580-1589, doi: 10.1101/gad.1941710.
Markman et al., "Targeting the PI3K/Akt/mTOR Pathway-Beyond Rapalogs", Oncotarget, vol. 1, No. 7, Nov. 2010, pp. 530-543.
Martin et al., "Chondrocyte Senescence, Joint Loading and Osteoarthritis", Clin Orthop Relat Res., 427 Suppl, Oct. 2004, pp. S96-S103.
Naylor et al., (2013) "Senescent Cells: A Novel Therapeutic Target for Aging and Age-Related Diseases", Clin Pharmacol Ther. 93(1): 105-116.
Momand et al. "The Mdm-2 Oncogene Product Forms a Complex with the p53 Protein and Inhibits p53-Mediated Transactivation", Cell, vol. 69, No. 7, Jun. 26, 1992, pp. 1237-1245.
No Author. Form S-1 Registration Statement as Filed with the Securities and Exchange Commission on Apr. 23, 2018, pp. 1-243.
No Author. Glossary of medical education terms, institute of International Medical Education. pp. 1-23. http://www.iime.ogr/glossary.htm [Accessed Mar. 2013].
Laberge et al., "Unit Dose of a Cis-Imidazoline for Treating an Osteoarthritic Joint by Removing Senescent Cells", Notice of Allowance and corresponding allowed claims received for U.S. Appl. No. 15/455,575, dated Aug. 18, 2017.
Laberge et al., "Treatment for Osteoarthritis by Intra-Articular Administration of a Cis-Imidazoline", Notice of Allowance and corresponding allowed claims received in U.S. Appl. No. 15/467,129, dated Aug. 3, 2017.

David, Nathaniel, "Chemical Entities that Kill Senescent Cells for Use in Treating Age-Related Disease", Office Action received for U.S. Appl. No. 15/069,769, dated May 17, 2017.
Laberge et al., "Treatment for Osteoarthritis by Intra-Articular Administration of a Cis-Imidazoline", Office Communication received for U.S. Appl. No. 15/467,129, dated Jul. 21, 2017.
Laberge et al., "Treatment for Osteoarthritis in a Joint by Administering a means for Inhibiting Mdm2" Office Communication received for U.S. Appl. No. 15/114,762, filed Sep. 14, 2017.
David et al., "Treatment of Joint Pain", Office Communication received for U.S. Appl. No. 15/481,129, dated Sep. 27, 2017.
Oliner et al., "Oncoprotein MDM2 Conceals the Activation Domain of Tumour Suppressor p53", Nature, vol. 362, No. 6423, Apr. 29, 1993, pp. 857-860.
Perry et al., "The Mdm-2 Gene is Induced in Response to UV light in a p53-Dependent Manner", Proc Natl Acad Sci USA., vol. 90, No. 24, Dec. 15, 1993, pp. 11623-11627.
Prieur et al., "Cellular Senescence in Vivo: A Barrier to Tumorigenesis", Curr Opin Cell Biol., vol. 20, No. 2, Apr. 2008, pp. 150-155, doi: 10.1016/j.ceb.2008.01.007, Epub Mar. 18, 2008.
Rodier et al., "Persistent DNA Damage Signalling Triggers Senescence-Associated Inflammatory Cytokine Secretion", Nat Cell Biol., vol. 11, No. 8, Aug. 2009, pp. 973-979, doi; 10.1038/ncb1909, Epub Jul. 13, 2009.
Saczewski et al., "Imidazoline Scaffold in Medicinal Chemistry: A Patent Review (2012-2015)", Expert Opin Ther Pat., vol. 26. No. 9, Jul. 20, 2016, pp. 1031-1048.
Shangary et al. "Temporal Activation of p53 by a Specific MDM2 Inhibitor is Selectively Toxic to Tumors and Leads to Complete Tumor Growth Inhibition", Proc Natl Acad Sci USA, vol. 105, No. 10, Mar. 11, 2008, pp. 3933-3938, doi: 10.1073/pnas.0708917105, Epub Mar. 3, 2008.
Taranto et al., "Detection of the p53 Regulator Murine Double-Minute Protein 2 in Rheumatoid Arthritis", J Rheumatol., vol. 32, No. 3. Mar. 2005, pp. 424-429.
Thomasova et al., "p53-Independent Roles of MDM2 in NF-κB Signaling: Implications for Cancer Therapy, Wound Healing, and Autoimmune Diseases", Neoplasia, vol. 14, No. 12. Dec. 2012, pp. 1097-1101.
Tovar et al., "MDM2 Small-Molecule Antagonist RG7112 Activates p53 Signaling and Regresses Human Tumors in Preclinical Cancer Models", Cancer Res., vol. 73, No. 8, Apr. 15, 2013, pp. 2587-2597, doi: 10.1158/0008-5472.CAN-12-2807, Epub Feb. 11, 2013.
Kirkland et al., "Killing Senescent Cells and Treating Senescence-Associated Conditions using a SRC Inhibitor and a Flavonoid", Non-Final Office Action received for U.S. Appl. No. 15/113,723, dated Jul. 26, 2018.
Laberge et al., "Methods and Compositions for Selectively Removing Senescent Cells from a Mixed Cell Population or Tissue by Inhibiting the P53 Negative Regulator Mouse Double Minute 2 Homolog (Mdm2)", Non-Final Office Action received for U.S. Appl. No. 15/455,630, dated May 22, 2018.
Laberge et al., "Methods and Compositions for Selectively Removing Senescent Cells from a Mixed Cell Population or Tissue by Inhibiting the P53 Negative Regulator Mouse Double Minute 2 Homolog (Mdm2)", Non-Final Office Action received for U.S. Appl. No. 15/455,630, dated Nov. 28, 2017.
Laberge et al., "A Method of Optimizing Conditions for Selectively Removing a Plurality of Senescent Cells from a Tissue or a Mixed Cell Population", First Action Interview Office Action Summary received for U.S. Appl. No. 15/455,684, dated Apr. 12, 2018.
Laberge et al., "A Method of Optimizing Conditions for Selectively Removing a Plurality of Senescent Cells from a Tissue or a Mixed Cell Population", First Action Interview Pilot Program, Pre-Interview Communication received for U.S. Appl. No. 15/455,684, dated Dec. 15, 2017.
David et al., "Treatment of Joint Pain", First Action Interview received for U.S. Appl. No. 15/481,129, dated Nov. 20, 2017.
Laberge et al., "Treating Pulmonary Conditions by Selectively Removing Senescent Cells from the Lung using an Intermittent Dosing Regimen", First Action Interview Pilot Program Pre-Interview Communication received for U.S. Appl. No. 15/955,542, dated Jun. 13, 2018.

(56) References Cited

OTHER PUBLICATIONS

UAMS News Bureau, "UAMS Research Findings Show Radiation, Aging Effects Can Be Cleared with Drug", Findings Published in Nature Medicine, Dec. 14, 2015, 2 pages, Available at <www.uamshealth.com/news>.

Uraoka et al., "Loss of bcl-2 during the Senescence Exacerbates the Impaired Angiogenic Functions in Endothelial Cells by Deteriorating the Mitochondrial Redox State", Hypertension, vol. 58, No. 2, Aug. 2011, pp. 254-263, doi: 10.1161/HYPERTENSIONAHA.111.17670, Epub Jul. 5, 2011.

Van Deursen, Jan M., "The Role of Senescent Cells in Ageing", Nature, vol. 509, No. 7501, May 22, 2014, pp. 439-446, doi: 10.1038/nature13193.

Vassilev et al., "In Vivo Activation of the p53 Pathway by Small-Molecule Antagonists of MDM2", Science, vol. 303, No. 5659, Feb. 6, 2004, pp. 844-848, Epub Jan. 2, 2004.

Wang, E., "Senescent Human Fibroblasts Resist Programmed Cell Death, and Failure to Suppress bcl2 is Involved", Cancer Res., vol. 55, No. 11, Jun. 1, 1995, pp. 2284-2292.

Wilson C., "Sweep Away Senile Cells", Life Extension Magazine, Mar. 2015, pp. 1-17.

Zauli et al., "Dasatinib Plus Nutlin-3 Shows Synergistic Antileukemic Activity in both p53 Wild-Type and p53 Mutated B Chronic Lymphocytic Leukemias by Inhibiting the Akt Pathway", Clin Cancer Res., vol. 17, No. 4, Feb. 15, 2011, pp. 762-770, doi: 10.1158/1078-0432.CCR-10-2572, Epub Nov. 24, 2010.

Zhang et al., "MDM2 Promotes Rheumatoid Arthritis via Activation of MAPK and NF-κB", Int Immunopharmacol., vol. 30, Dec. 2, 2015, pp. 69-73.

Zhao et al., "Small Molecule Inhibitors of MDM2-p53 and MDMX-p53 interactions as New Cancer Therapeutics", BioDiscovery, vol. 8, No. 4, 2013, 15 pages.

Zhu et al., "Identification of a Novel Senolytic Agent, Navitoclax, Targeting the Bcl-2 Family of Anti-Apoptotic Factors", Aging Cell, vol. 15, No. 3, Jun. 2016, pp. 428-435, Epub Mar. 18, 2016.

Zhu et al., "The Achilles' Heel of Senescent Cells: From Transcriptome to Senolytic Drugs", Aging Cell, vol. 14, No. 4, Aug. 2015, pp. 644-658, Epub Apr. 22, 2015.

Co-Pending U.S. Application: Laberge et al., "Unit Dose of an Aryl Sulfonamide that is Effective for Treating Eye Disease and Averting Potential Vision Loss", U.S. Appl. No. 16/007,880, filed Jun. 13, 2018.

Co-Pending U.S. Application: Laberge et al., "Treatment for Idiopathic Pulmonary Fibrosis and Chronic Obstructive Pulmonary Disease", U.S. Appl. No. 15/808,417, filed Nov. 9, 2017.

Uthman et al., "Intra-Articular Therapy in Osteoarthritis" Postgrad. Med. J. (2003) vol. 79. pp. 449-453.

Hashimoto T. et al., "Inhibition of MDM2 attenuates neointimal hyperplasia via suppression of vascular proliferation and inflammation" Cardiovascular Research, 91(4). pp. 711-719, (2011).

Collado M. et al., "Inhibition of the Phosphoinositide 3-kinase Pathway Induces a Senescence-Like Arrest Mediated by p27Kip1" The Journal of Biological Chemistry, 275(29), pp. 21960-21968. (2000).

Hartung D. et al., "Resolution of Apoptosis in Atherosclerotic Plaque by Dietary Modification and Statin Therapy" Journal of Nuclear Medicine, 46(12) 2051-6, (2005).

Suga S. et al., "An Inhibitory Effect on Cell Proliferation by Blockage of the MAPK/Estrogen Receptor/MDM2 Signal Pathway in Gynecologio Cancer." Gynecol Oncol. May 2007; 105(2): 341-50.

England B. et al., ". Current Understanding of the Role and Targeting of Tumor Suppressor p53 in Glioblastoma Multiforme" Tumour Biol. Aug. 2013;34(4):2063-74.

Nag S. et al., "The MDM2-p53 Pathway Revisited" J Biomed Res. Jul. 2013 (4):254071.

Setten RL. et al., "The Current State and Fturue of Directions of RNAi Therapeutics" Nat Rev Drug Discov. Jun. 18, 2019(6):421-446.

Angart et al., "Design of siRNA Therapeutics from the Molecular Scale" Pharmaceuticals, 6(4), Jan. 24, 2013, pp. 440-468.

Blagosklonny, "Aging and Immortality: Quasi-Programmed Senescence and It's Pharmacologic Inhibition," Cell Cycle 5(18), Sep. 15, 2006, pp. 2087-2102.

Fellman et al., "Functional Identification of Optimized RNAi Triggers Using a Massively Parallel Sensor Assay" Molecular Cell 41, Mar. 18, 2011, pp. 733-746.

Kwok et al., "Determination of In Vivo RNA Structure in Low-Abundance Transcripts" Nature Communications, 4:2971, Dec. 16, 2013, 12 pages.

* cited by examiner

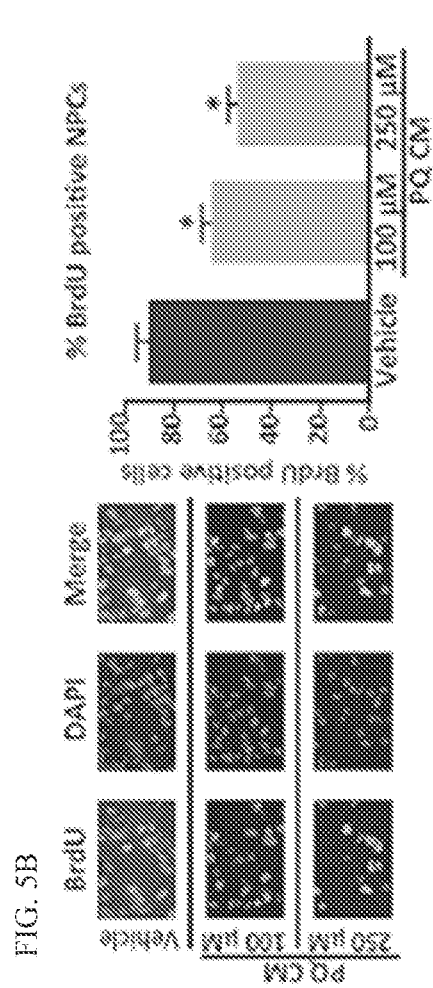
FIG. 5A
FIG. 5B
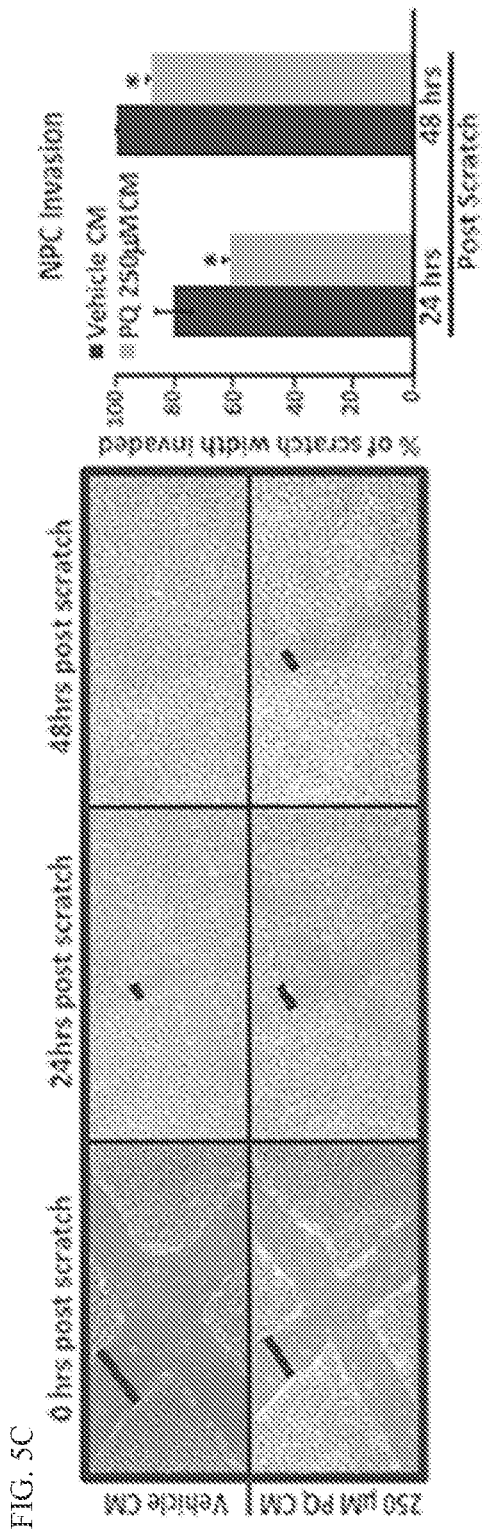
FIG. 5C

TREATMENT OF A SENESCENCE-ASSOCIATED OCULAR DISEASE OR DISORDER USING A Bcl-xL SELECTIVE INHIBITOR

CROSS-REFERENCE TO RELATED APPLICATIONS

This application is a continuation of U.S. patent application Ser. No. 17/548,004, filed Dec. 10, 2021, which is a continuation of U.S. patent application Ser. No. 16/403,389, filed May 3, 2019, which is a continuation-in-part of U.S. patent application Ser. No. 15/950,965 (now U.S. Pat. No. 10,413,542), filed Apr. 11, 2018, which is a continuation of U.S. patent application Ser. No. 15/114,762 (now U.S. Pat. No. 9,993,472), filed Jul. 27, 2016, which is the U.S. National Stage of PCT/US2015/013387 (published as WO 2015/116740), which claims the priority benefit of provisional applications 61/932,704, filed Jan. 28, 2014; 61/932,711, filed Jan. 28, 2014; 61/979,911, filed Apr. 5, 2014; 62/002,709, filed May 23, 2014; 62/042,708, filed Aug. 27, 2014, 62/044,664, filed Sep. 2, 2014; 62/057,820, filed Sep. 30, 2014; 62/057,825, filed Sep. 30, 2014; 62/057,828, filed Sep. 30, 2014; 62/061,627, filed Oct. 8, 2014; and 62/061,629, filed Oct. 8, 2014.

STATEMENT OF GOVERNMENT INTEREST

This invention was made with government support under AG009909, AG017242, AG041122, and AG046061 awarded by the National Institutes of Health. The government has certain rights in the invention.

The aforelisted applications are all hereby incorporated herein by reference in their entirety for all purposes, including but not limited to the preparation and use of senolytic agents to treat atherosclerosis.

FIELD OF THE INVENTION

The technology disclosed and claimed below relates generally to the fields of neurobiology and senescent cells. In particular, this disclosure provides a family of compounds and techniques that can be used for treating Parkinson's disease by eliminating senescent cells implicated in the underlying pathophysiology and symptomatology.

BACKGROUND

Parkinson's disease (PD) is a long-term degenerative disorder of the central nervous system that mainly affects the motor system. Early in the disease, the most obvious symptoms are shaking, rigidity, slowness of movement, and difficulty with walking. Thinking and behavioral problems may also occur. Dementia becomes common in the advanced stages of the disease, along with depression and anxiety.

The possible role of environmental stress, aging and glial cell senescence as a mechanistic link to Parkinson's disease was suggested by Chinta, Campisi, Anderson et al. in J Intern Med. 2013 May; 273(5):429-36. The benefits of clearing senescent cells in the treatment of Parkinson's disease was first described in U.S. Pat. No. 9,993,472 (previously published as WO 2015/116740), to which this application claims priority. M. Reissland et al. subsequently showed that the loss of SATB1 (a DNA binding protein associated with Parkinson's disease) induces a p21 dependent cellular senescence phenotype in dopaminergic neurons. bioRxiv, Oct. 25, 2018. Chinta, Campisi, Anderson et al. published an article on induction of cellular senescence that contributes to neuropathology linked to Parkinson's disease. Cell Rep. 2018 Jan. 23; 22(4):930-940, 2018. These and other studies, commentaries, and grant applications demonstrate a growing interest in the role of senescent cells in Parkinson's disease since the publication of WO 2015/116740.

Before the advent of the invention provided in this disclosure, there has been no cure for Parkinson's disease. Currently available treatment is directed at improving symptoms: typically with the antiparkinson medication levodopa (L-DOPA), with dopamine agonists being used once levodopa becomes less effective. Surgery to place microelectrodes for deep brain stimulation has been used to reduce motor symptoms in severe cases where drugs are ineffective.

Parkinson's disease is the second most common age-related neurodegenerative disorder after Alzheimer's disease. An estimated seven million to 10 million people worldwide have the disease. The prevalence of the disease ranges from 41 people per 100,000 in the fourth decade of life to more than 1,900 people per 100,000 among those 80 and older. An estimated 4 percent of people with Parkinson's are diagnosed before the age of 50.

SUMMARY

This invention provides a new paradigm for treatment of Parkinson's disease (PD) by eliminating senescent cells that reside in or around the site of the disease pathophysiology. Exposure to the herbicide paraquat (PQ) increases the risk for developing Parkinson's disease. The data in this disclosure show that PQ induces a senescence arrest and SASP in astrocytes, in culture and in vivo in mice, and senescent cell markers were present in astrocytes in midbrain tissue from PD patients. In a transgenic mouse model, senescent cell ablation protected against PQ-induced PD-like neuropathology.

Removal of senescent cells from affected sites using small molecule agents that specifically target senescent cells can help prevent or ameliorate one or more signs and symptoms of Parkinson's disease. The same technology can be adapted for treatment of other neurological conditions caused or mediated by senescent astrocytes, mutatis mutandis. Such conditions include amyotrophic lateral sclerosis (ALS), conditions characterized by the presence of activated microglia, and other age-related neurological deficiencies.

Features of the technology of the invention are provided in the sections below and in the appended claims.

DRAWINGS

Figure 1B:
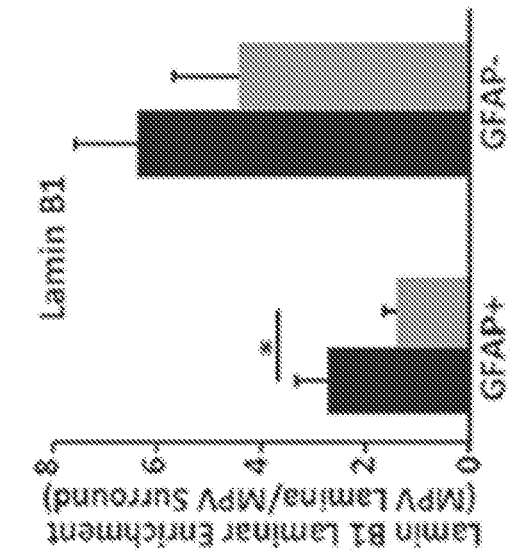
Figure 1C:
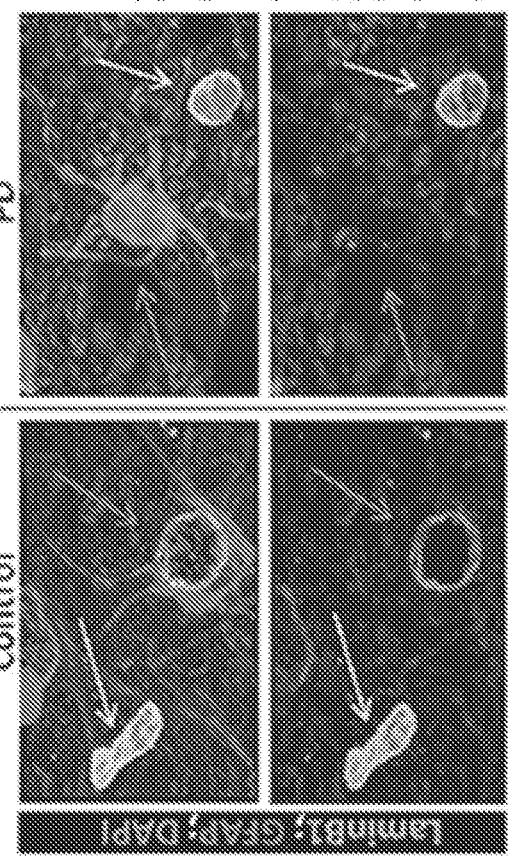
Figure 2A:
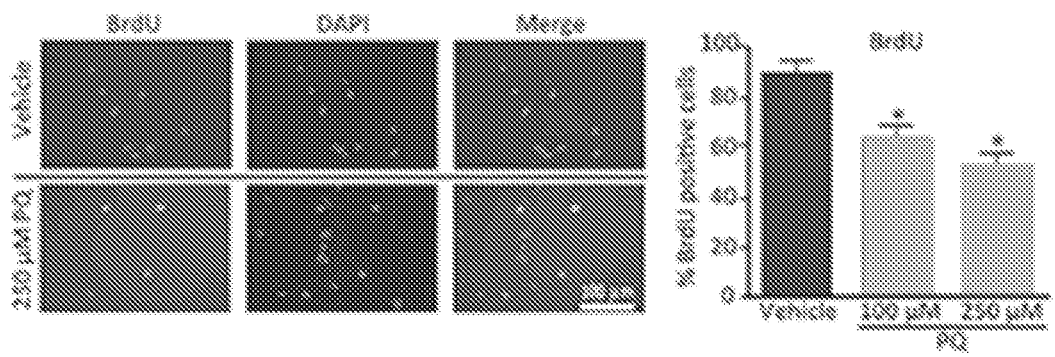
Figure 2B:
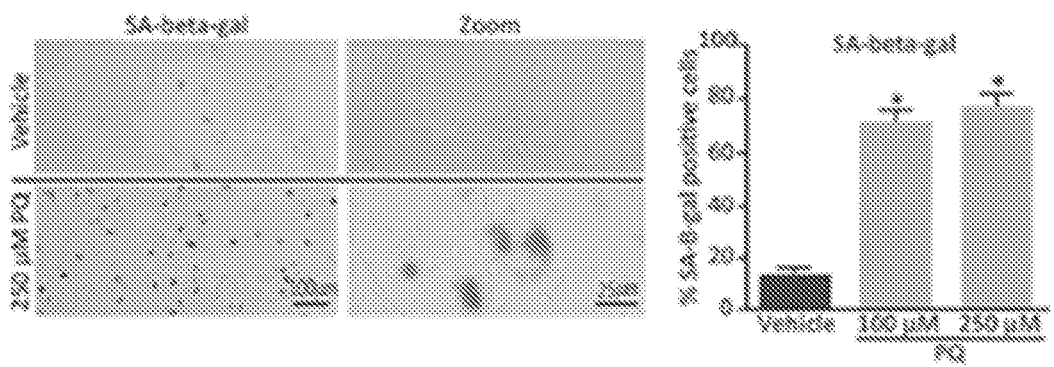
Figure 2C:
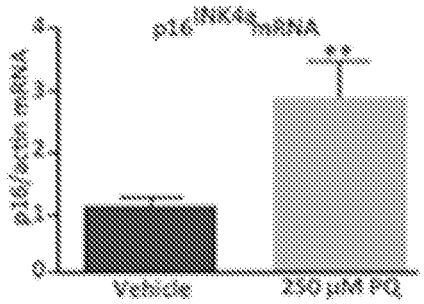
Figure 2D:
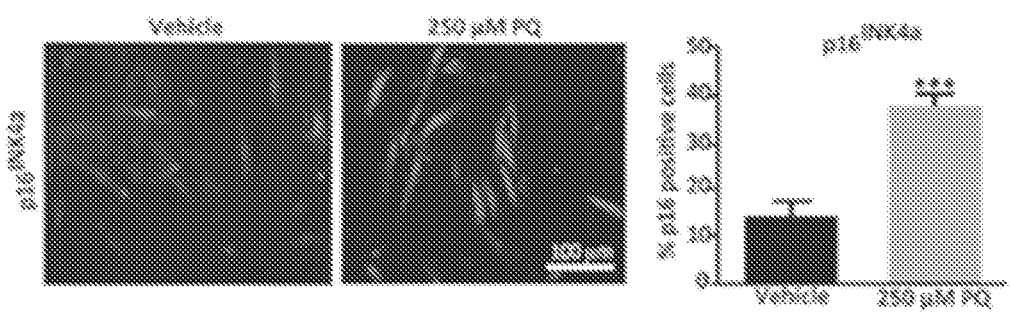
Figure 2E:
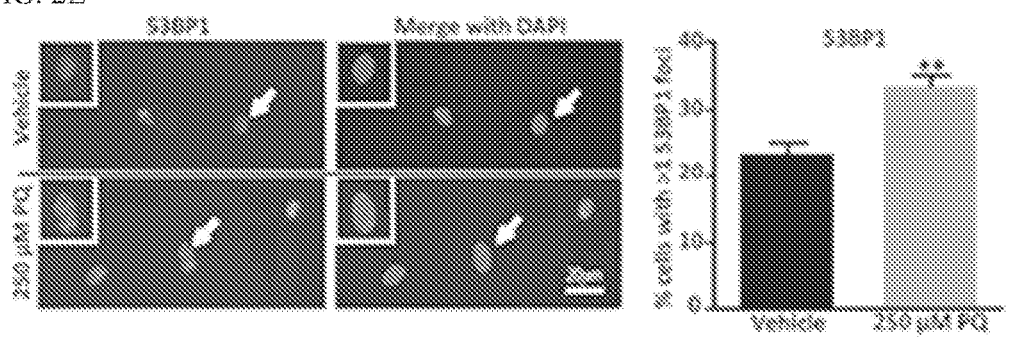
Figure 2F:
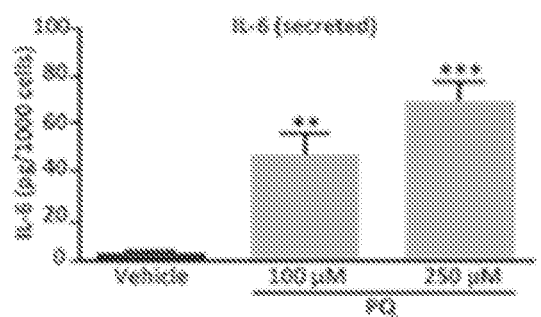

FIGS. 1A, 1B, and 1C: Senescence markers in substantia nigra (SN) isolated from PD and age-matched control individuals. RNA isolated from autopsied SN tissues from PD and control individuals (n=5 each) were analyzed for p16INK4a (FIG. 1A) and several SASP factors (IL-1alpha, IL-6, IL-8, MMP-3) mRNA levels by qPCR; transcripts were normalized to actin and are shown as fold change over control levels; *p<0.05 and #p<0.005. (FIG. 1B) Representative immunofluorescence images showing expression of LMNB1 in GFAP+ astrocytes (dark arrows) in the SN of PD tissue (right panels) compared to age matched control tissue (left panels). Neighboring GFAP– cells (light arrows) retain LMNB1 expression in PD tissue. (FIG. 1C) Quantification of image data showing that compared to control (black bar; n=5 individuals), PD (grey bar; n=5 individuals) is associated with significantly decreased LMNB1 levels in GFAP+, but not GFAP−, cells; *p<0.05; paired t test.

FIGS. 2A to 2F: PQ induces senescent phenotypes in cultured human astrocytes. (FIG. 2A) BrdU labeling in human astrocytes treated with PQ (or vehicle) as described in FIG. 2B. (FIG. 2B) Human astrocytes treated with 100 or 250 uM PQ (or vehicle) for 24 h were assayed 7 d later for SA-beta-gal activity. (FIG. 2C) Quantitative PCR of $p16^{INK4a}$ mRNA levels, normalized to actin, in cultured human astrocytes treated with PQ or vehicle. (FIG. 2D) Immunostaining for $p16^{INK4a}$ in human astrocytes treated with PQ (or vehicle) as described in FIG. 2B. (FIG. 2E) Immunostaining for and 53BP1 in cells described in FIG. 2B. Nuclei were counterstained with DAPI; white arrows show punctate nuclear foci. (FIG. 2F) Secreted IL-6 levels measured by ELISA in conditioned media from non-senescent (vehicle) and senescent (PQ-treated) astrocytes. n=2 for all experiments.

FIGS. 3A-3D: Paraquat induces morphological features of senescence and arrests proliferation in both fibroblasts and astrocytes. (FIGS. 3A-3B) DAPI stained human fibroblasts (top panels; black bars) and astrocytes (bottom panels; grey bars) and quantification. (FIG. 3A) Human fibroblasts and astrocytes respond to PQ with a decrease in Ki67+ cells, compared to vehicle treated controls. (FIG. 3B) Human fibroblasts and astrocytes respond to PQ (1 mM and 300 uM, respectively) with increased nuclear size. (FIG. 3B) The increase in nuclear size is similar to that obtained when cells were exposed to 10 Gy X-rays. (FIG. 3A) The decrease in the percentage of Ki67+ cells is similar to that obtained when cells were exposed to 10 Gy X-rays. (FIG. 3C) LMNB1 expression in human fibroblasts. (FIG. 3D) Fluorescent images of human fibroblasts culture at differing concentrations of PQ juxtaposed to human and 3MR mouse astrocyte cultures grown in differing concentrations of PQ.

Figure 4B:
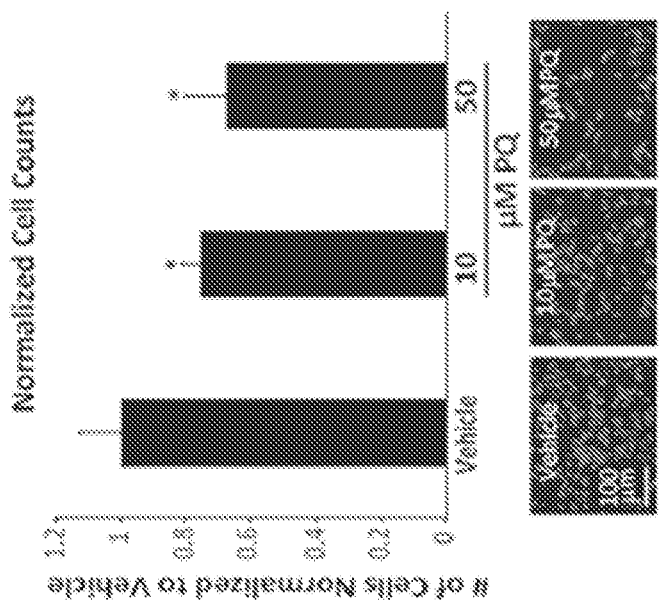
Figure 4A:
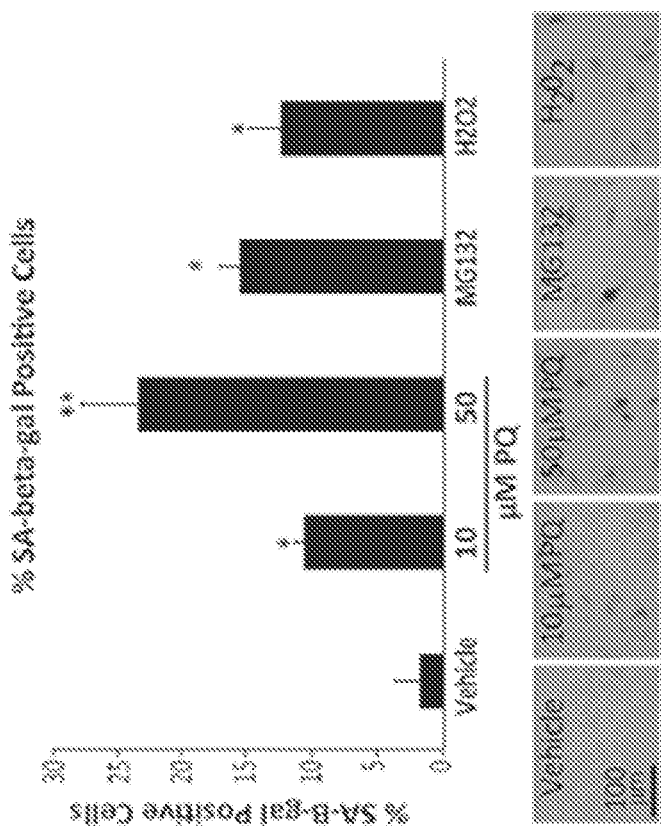

FIGS. 4A and 4B show SA-βgal activity in human fibroblasts. (FIG. 4B) The cell counts in FIG. 4A normalized to the Vehicle used.

FIGS. 5A to 5C: Factors secreted by senescent human astrocytes have detrimental effects. (FIG. 5A) Conditioned media (CM) from human astrocytes induced to senesce by PQ was added to dopaminergic neurons and cell viability was assessed using the MTT assay. (FIG. 5B and FIG. 5C) The CM described in FIG. 5A was added to hESC-derived neural progenitor cells (NPCs). (FIG. 58) Proliferation assessed by BrdU positivity and cell migration was assessed by the time required to fill a cleared area in the culture dish (scratch assay in FIG. 5C); black lines in FIG. 5C indicate the width of the uninvaded area, which was used for quantification N=2 for all experiments.

FIGS. 6A-6D: PQ-induced senescence is prevented by GCV in p16-3MR mice. (FIG. 6A) RNA was isolated from the striatum and analyzed for expression $p16^{INK4a}$ and IL-6 mRNA. *p<0.05, saline vs PQ; #p<0.05, PQ vs PQ+GCV. (FIG. 6B) Representative images of immunofluorescence in p16-3MR mice showing expression of LMNB1 in GFAP+ astrocytes in vivo in the SN, as evidenced by tyrosine hydroxylase staining (magenta); nuclei were DAPI stained. Mice were treated with 1) saline; 2) PQ; 3) GCV alone; or 4) PQ+GCV. (FIG. 6B) Quantification of LMNB1 fluorescence in the nuclear lamina in the 4 conditions is shown on the right. (FIG. 6C) Representative immunofluorescence images in p16-3MR mice showing HMGB1 nuclear localization with similar counter stains as in FIG. 6B. (FIG. 6C) The 4 panels show an example image from each of 4 conditions in FIG. 6B. (FIG. 6C) On the right, quantification of HMGB1 fluorescence in the nucleus in the 4 conditions. n=4 individuals/condition for: saline, PQ+GCV and GCV and n=3 individuals for PQ. (FIG. 6D) Representative immunofluorescence image showing reduced expression of LMNB1, in GFAP+ astrocytes (dark arrows) in the SN of a PQ treated mouse (right panels) compared to saline injected control (left panels). Neighboring GFAP− cells (light arrows) retain LMNB1 expression in PQ injected mice. (FIG. 6D) On the right, quantification of image data compared to control ("saline"; black bar, n=4 individuals), PQ (grey bar; n=3 individuals); *p<0.05; unpaired TTEST.

Figure 7A:
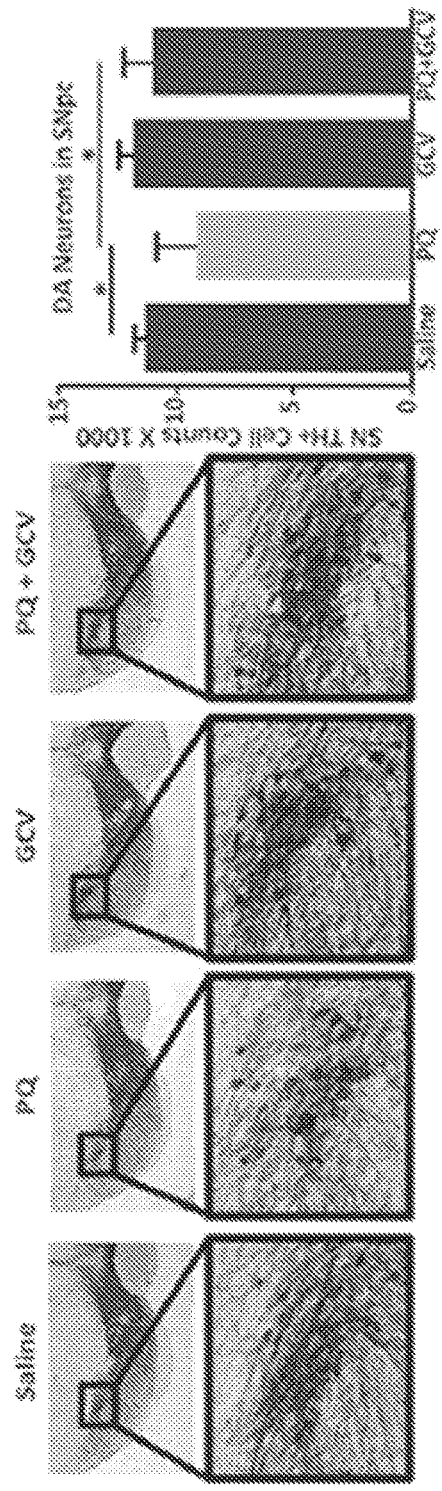
Figure 7B:
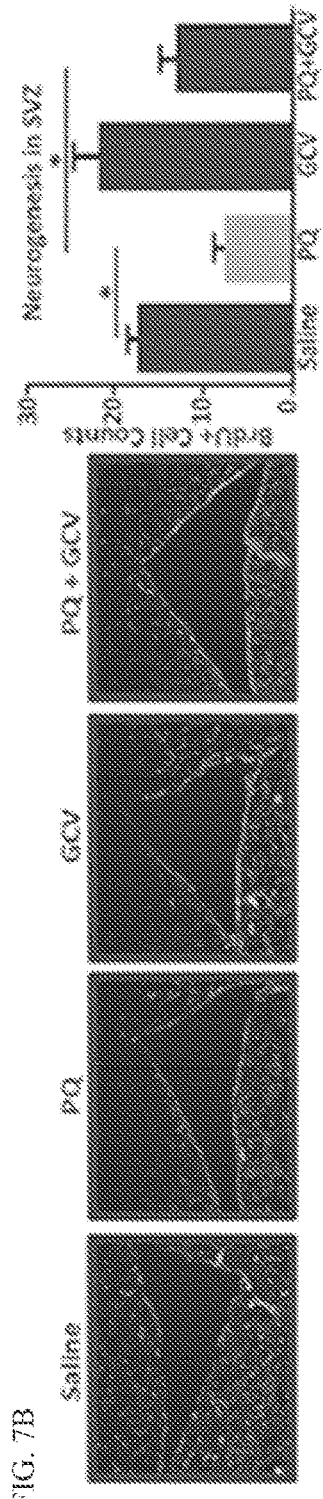
Figure 7C:
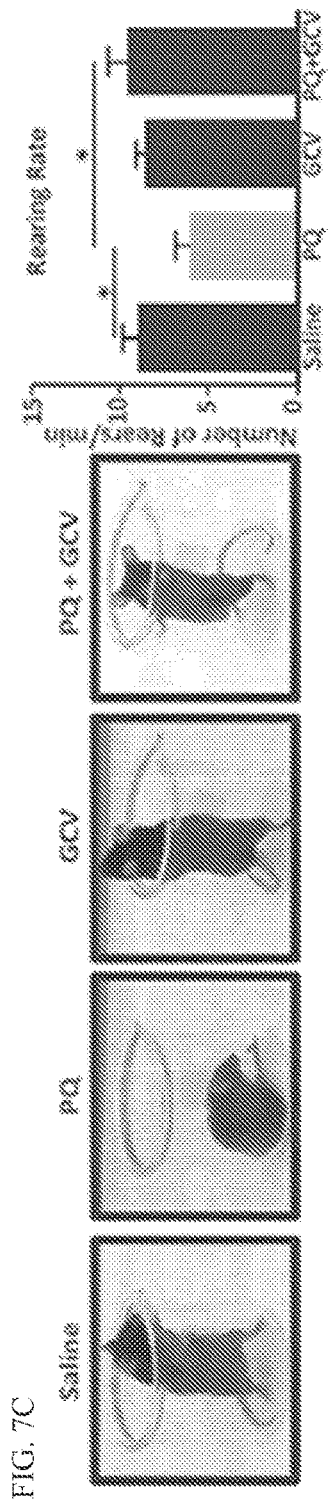
Figure 8B:
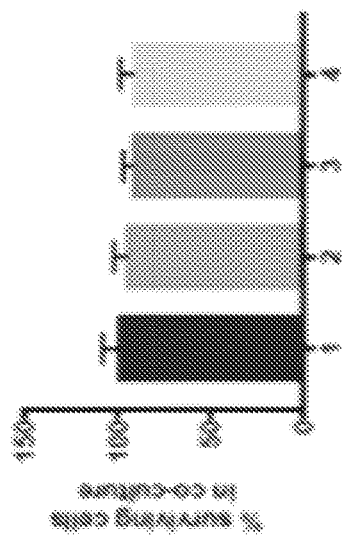
Figure 8D:
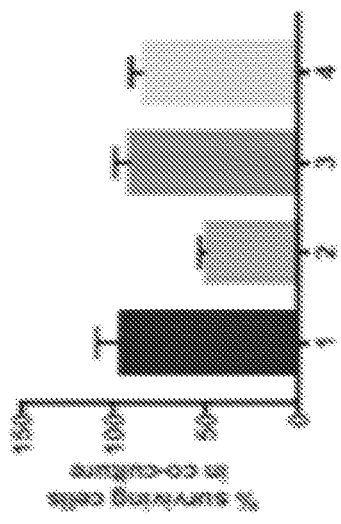
Figure 8A:
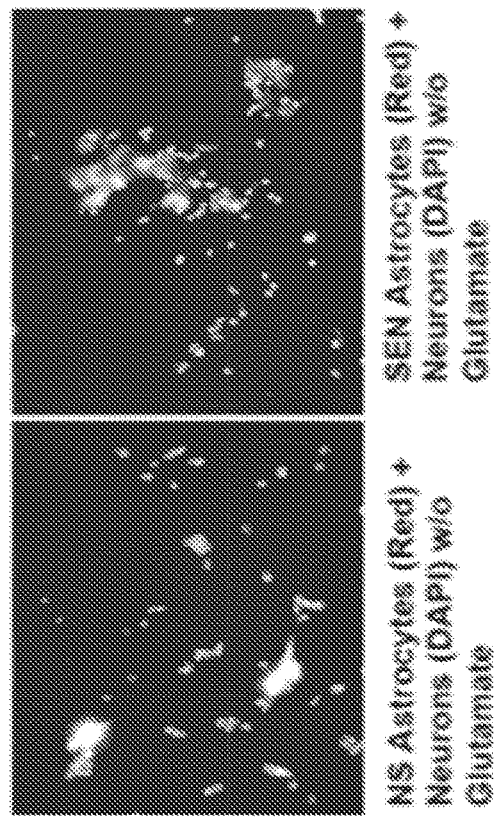
Figure 8C:
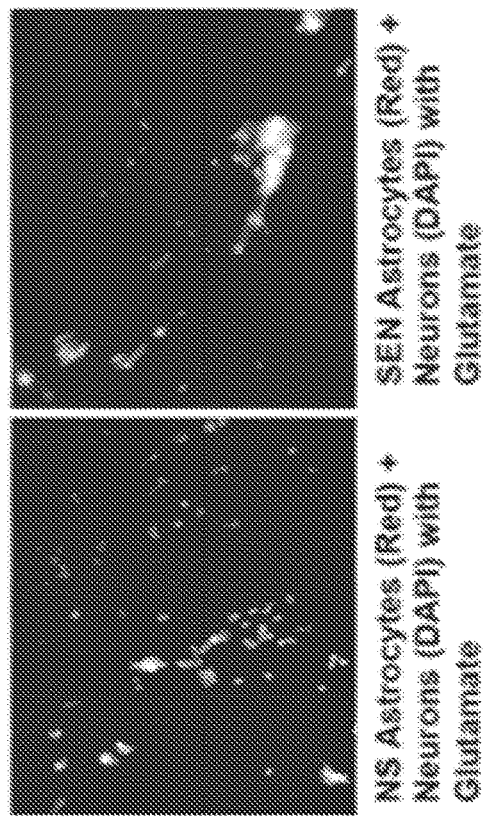

FIGS. 7A and 7C: Eliminating senescent cells prevents loss of dopaminergic neurons in mice. (FIG. 7A) Stereological SN TH+ cell counts were performed on PQ-treated and saline-treated p16-3MR mice treated with GCV or saline; n=6 per condition. Data are expressed as total SN TH+ cell numbers per animal. #=p<0.05, PQ-treated vs controls; *=p<0.05 PQ vs PQ+GCV. Cell counts were verified by Nissl staining (not shown). (FIG. 7C) Prior to sacrifice, locomotor activity was monitored using the cylinder test which measures rearing rate; n=6 per condition; #=p<0.05, PQ-treated vs control; *=p<0.05 PQ vs PQ+GCV.

FIG. 7B: Depression of neurogenesis by PQ is prevented by clearing senescent cells. Neurogenesis was assessed by counting BrdU positive cells in the subventricular zone (SVZ) in the 4 cohorts, as described by (Peng et al.). (FIG. 7B) Representative sections showing BrdU-positive cells in the SVZ region. (FIG. 7B) Quantitation of BrdU-positive cells in the SVZ region. n=6 mice per condition, #=p<0.05, PQ-treated vs controls; *=p<0.05, PQ vs PQ+GCV. Values are reported as BrdU+ cells per field averaged from 5 fields.

FIGS. 8A to 8D show that neurons cocultured with SEN (senescent) astrocytes die in the presence of 10 mM glutamate. In panels (FIG. 8A) and (FIG. 8B): Neurons (only DAPI-stained cells) were co-cultured with NS or SEN astrocytes (CMPTX+DAPI-stained cells) in neuronal media. The co-cultures were then treated for 24 h with control media without glutamate. Panel (FIG. 8A) shows the fluorescent images; panel (FIG. 8B) shows cell quantification. In panels (FIG. 8C) and (FIG. 8D): Neurons were co-cultured with NS or SEN astrocytes in neuronal media. In this case, the co-cultures were then treated for 24 h with media containing 10 mM glutamate. Panel (FIG. 8C) shows the fluorescent images; panel (FIG. 8D) shows cell quantification.

DETAILED DESCRIPTION

This invention is based on the discovery that senescent cells (particularly senescent astrocytes) play a role in the pathophysiology of Parkinson's disease (PD).

Advantages of Treating Parkinson's Disease by Clearing Senescent Cells

The role of senescent cells in promoting or mediating Parkinson's diseases provides an approach to treatment with a number of advantages for the managing clinician.

Since senescent cells are non-proliferative, eliminating senescent cells has the potential for a clinically beneficial effect that persists for an extended time between episodes of treatment. Features of the condition mediated by senescent cells resolve at least until senescent cells re-accumulate. Since senescent cells are likely to accumulate slowly (given the nature of age related diseases is to evolve over a period of many years), the effects of a single treatment or treatment cycle may last for weeks, months, or years.

To the extent that senescent cells exacerbate other types of pathology such as inflammation or tissue breakdown, the long-lasting effect of senolysis provides a window in which such pathology is held at bay, potentially giving the tissue a chance for repair. This means that senescent cell medicine has the potential not just to halt progression of Parkinson's disease but may allow some degree of reversal of the disease and its symptoms for the benefit of the patient.

By addressing the early pathology in a disease, senolytic medicine can be an important adjunct to other types of therapy that are administered to treat later stage pathology, or to relieve the symptoms that result from the condition. The two modes of therapy potentially work synergistically or additively to reduce the burden, frequency and side effects of either mode administered separately.

Manifestations of Parkinson's Disease

Parkinson's disease (PD) is the second most common neurodegenerative disease. It is a disabling condition of the brain characterized by slowness of movement (bradykinesia), shaking, stiffness, and in the later stages, loss of balance. Many of these symptoms are due to the loss of certain nerves in the brain, which results in the lack of dopamine. This disease is characterized by neurodegeneration, such as the loss of about 50% to 70% of the dopaminergic neurons in the substantia nigra pars compacta, a profound loss of dopamine in the striatum, or the presence of intracytoplasmic inclusions (Lewy bodies), which are composed mainly of alpha-synuclein and ubiquitin. Senescence of dopamine-producing neurons is thought to contribute to the observed cell death in PD through the production of reactive oxygen species (Cohen et al., J. Neural Transm. Suppl. 19:89-103 (1983)). Parkinson's disease also features locomotor deficits, such as tremor, rigidity, bradykinesia, or postural instability. Subjects at risk of developing Parkinson's disease include those having a family history of Parkinson's disease and those exposed to pesticides (e.g., rotenone or paraquat), herbicides (e.g., agent orange), or heavy metals.

Methods for detecting, monitoring or quantifying neurodegenerative deficiencies or locomotor deficits associated with Parkinson's diseases are known in the art, such as histological studies, biochemical studies, and behavioral assessment (US 2012/0005765 A1). There are five primary motor symptoms of Parkinson's disease: tremor, rigidity, bradykinesia (slow movement), postural instability (balance problems), and walking/gait problems.

Demonstrating a Role for Senescent Cells in Causing or Mediating Parkinson's Disease Environmental exposures can result in brain injury resembling PD. One of the best studied of these environmental agents is the herbicide PQ. This agent is strongly linked in epidemiological studies to PD in humans, and has been extensively used to investigate mechanisms underlying PD in animal models. See, for example, McCormack. A. L., M. Thiruchelvam, A. B. Manning-Bog, C. Thiffault, J. W. Langston, D. A. Cory-Slechta and D. A. DiMonte (2002). "Environmental risk factors and Parkinson's disease: selective degeneration of nigral dopaminergic neurons caused by the herbicide paraquat." Neurobiol Dis in press. Thiruchelvam, M., E. K. Richfield, B. M. Goodman, R. B. Baggs and D. A. Cory-Slechta (2002). "Developmental exposure to the pesticides paraquat and maneb and the Parkinson's disease phenotype." Neurotoxicology 23(4-5): 621-633. Pezzoli. G. and E. Cereda (2013). "Exposure to pesticides or solvents and risk of Parkinson disease." Neurology 80(22): 2035-2041.

PQ is a free radical generator due to its ability to redox cycle, and ultimately causes oxidative stress). Oxidative stress can induce cellular senescence in several cell types. We therefore hypothesized that one mechanism by which PQ might contribute to PD is by inducing cellular senescence in proliferative-competent cells in the brain. Chinta, S. J., G. Woods, A. Rane, M. Demaria, J. Campisi and J. K. Andersen (2015). "Cellular senescence and the aging brain." Exp Gerontol 68: 3-7.

To test this idea, we examined the effect of PQ on cultured human astrocytes. We chose astrocytes because they are the predominant cell type in the mammalian brain that is capable of proliferation, and astrocytes expressing senescence markers were recently shown to increase during aging and in Alzheimer's disease (AD). The examples below show that PQ is not only a potent inducer of senescence in cultured human astrocytes, but factors secreted by these cells have detrimental effects on both cultured human DAergic neurons and NPCs.

To address whether senescent cells causatively contribute to the PD neuropathologies associated with PQ exposure, we examined the impact of eliminating senescent cells in vivo in mice following PQ exposure. Strikingly, removing senescent cells during the course of ongoing PQ treatment prevented PD-related neuropathologies. Importantly, the senescence markers observed following PQ administration were also elevated in astrocytes in SN tissue from autopsied human PD brain samples, suggesting that our findings are relevant to the human disease.

Astrocytes provide structural, metabolic and trophic support to neurons. However, when astrocytes adopt pro-inflammatory phenotypes they can compromise neuronal health and contribute to age-related neurodegeneration and decrements in brain function in vivo. The data provided below show that an important contributor to the neuroinflammation associated with PD is astrocyte senescence and the accompanying SASP.

Other neurodegenerative diseases besides PD are linked to aging, and so astrocytes and other proliferative cell types in the brain might undergo senescence during aging and contribute to these diseases. For instance, astrocyte senescence has been linked to the degeneration of motor neurons in Amyotrophic Lateral Sclerosis (ALS), and activated microglia in the aged brain, a well-known pathology associated with PD and AD might in fact be senescent. Interestingly, repeated exposure to lipopolysaccharide, which models chronic inflammation, triggers senescence of BV2 (immortalized murine microglia) cells.

Further, although our cell culture data suggest post-mitotic neurons do not mount a classic senescence response upon genotoxic stress, senescence markers have been reported in post-mitotic neurons in the aging human and mouse brain. p16INK4a expression increases with age in NPCs, although, when induced to senesce in culture, NPCs tend to differentiate into senescent astrocytes.

Suitable Senolytic Agents

Compounds that may be useful for clearing senescent cells in the brain for purposes of treating Parkinson's disease according to this invention include Bcl-2 inhibitors, Bcl-xL inhibitors. MDM2 inhibitors, and Akt inhibitors. See U.S. Pat. No. 9,849,128 (Laberge et al.) and pre-grant publication WO 2015/116740 (Laberge et al.).

Candidate senolytic agents that act as Bcl-2. Bcl-w, and Bcl-xL inhibitors can be characterized as a benzothiazole-hydrazone, an amino pyridine, a benzimidazole, a tetrahydroquinolin, or a phenoxyl compound. Examples of compounds that inhibit Bcl isoforms include WEHI 539, A 1155463, ABT-737, and ABT-263 (Navitoclax).

A genus of Bcl family inhibitors that includes ABT-263 may be represented by Formula (II):

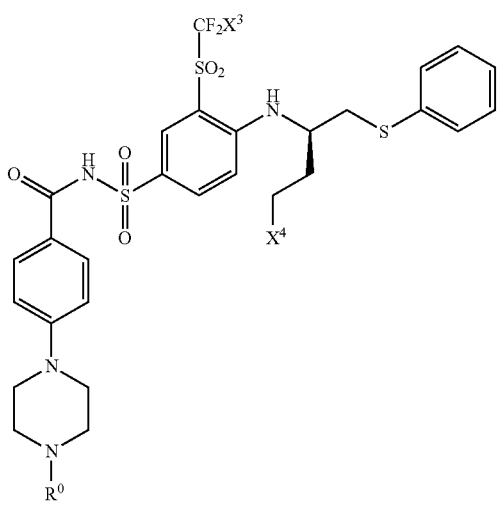

wherein $X^3$ is Cl or F;
$X^4$ is azepan-1-yl, morpholin-4-yl, 1,4-oxazepan-4-yl, pyrrolidin-1-yl, $N(CH_3)_2$, $N(CH_3)(CH(CH)_2)$, 7-azabicyclo[2.2.1]heptan-1-yl or 2-oxa-5-azabicyclo[2.2.1]hept-5-yl, and $R^0$ is

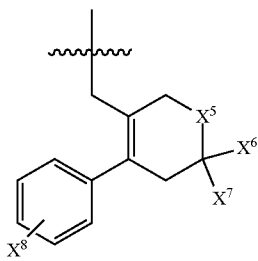

wherein $X^5$ is $CH_2$, $C(CH_3)_2$, or $CH_2CH_2$; $X^6$ and $X^7$ are both hydrogen or are both methyl; and $X^8$ is F, Cl, Br or I; or $X^4$ is azepan-1-yl, morpholin-4-yl, pyrrolidin-1-yl, $N(CH_3)(CH(CH_3)_2)$ or 7-azabicyclo[2.2.1]heptan-1-yl, and $R^0$ is

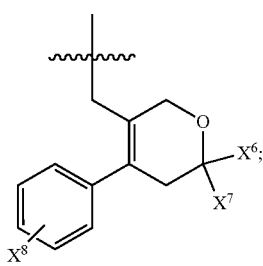

or
$X^4$ is $N(CH_3)_2$ or morpholin-4-yl, and $R^0$ is

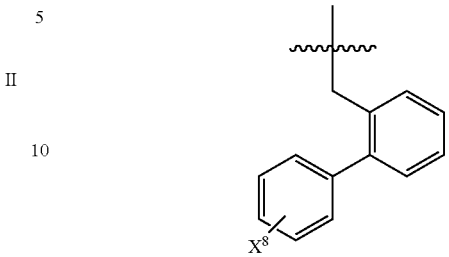

Candidate senolytic agents that act as MDM2 inhibitors can be characterized as a cis-imidazoline, a dihydroimidazothiazole, a spiro-oxindole, a benzodiazepine, or a piperidinone. Candidate in MDM2 include Nutlin-1, Nutlin-2, Nutlin-3a, RG-7112, RG7388, R05503781. DS-3032b, MI-63, MI-126, MI-122, MI-142, MI-147, MI-18, MI-219, MI-220, MI-221, MI-773, 3-(4-chlorophenyl)-3-((1-(hydroxymethyl)cyclopropyl)methoxy)-2-(4-nitrobenzyl)isoindolin-1-one, Serdemetan, AM-8553, CGM097, R0-2443, and R0-5963.

A genus of MDM2 inhibitors that includes nutlin-3a may be represented by Formula (I):

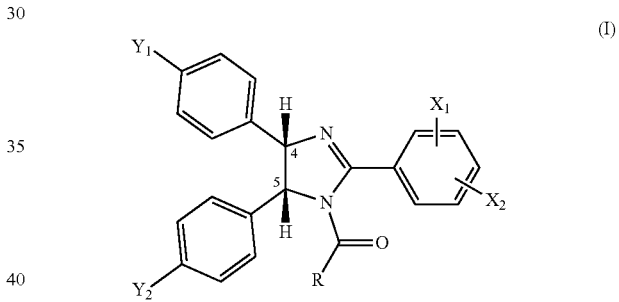

wherein R is selected from saturated and unsaturated 5- and 6-membered rings containing at least one hetero atom, wherein the hetero atom is selected from S, N and O and is optionally substituted with a group selected from lower alkyl, cycloalkyl, —C=O—$R_1$, hydroxy, lower alkyl substituted with hydroxy, lower alkyl substituted with lower alkoxy, lower alkyl substituted with —$NH_2$, lower alkyl substituted with —C=O—$R_1$, N-lower alkyl, —$SO_2CH_3$, =O and —$CH_2C$=$OCH_3$;
$R_1$ is selected from hydrogen, lower alkyl, —$NH_2$, —N-lower alkyl, lower alkyl substituted with hydroxy, lower alkyl substituted with —$NH_2$, and a 5- or 6-membered saturated ring containing at least one hetero atom selected from S, N and O;
$X_1$ and $X_2$ are each independently selected from hydrogen, lower alkoxy, —$CH_2OCH_3$, —$CH_2OCH_2CH_3$, —$OCH_2CF_3$, and —$OCH_2CH_2F$; and
$Y_1$ and $Y_2$ are each independently selected from —Cl, —Br, —$NO_2$, —C≡N, and —C≡CH;
wherein the composition contains a formulation of the compound suitable for administration to subject who has atherosclerosis; and
wherein the formulation of the composition and the amount of the compound in the unit dose configure the unit dose to be effective in treating the atherosclerosis by eliminating p16 positive senescent cells in or around atherosclerotic plaques in the subject, thereby stabilizing the plaques so as to reduce the risk that the plaques will rupture.

Candidate senolytic agents that act as inhibitors of Akt (protein kinase B) are the competitive Akt inhibitors CCT128930, GDC-0068, GSK2110183 (afuresertib), GSK690693, and AT7867; the lipid-based Akt inhibitors Calbiochem Akt Inhibitors I, II and III, PX-866, and Penfosine (KRX-0401); the pseudosubstrate inhibitors vKTide-2 T and FOXO3 hybrid; allosteric inhibitors of the Akt kinase domain, particularly MK-2206 (8-[4-(I-aminocyclobutyl)phenyl]-9-phenyl-2H-[1,2,4]triazolo[3,4-f][1,6]naphthyridin-3-one; dihydrochloride); the antibody GST-anti-Akt1-MTS; the compounds that interact with the PH domain of Akt Triciribine and PX-316; and other compounds exemplified by GSK-2141795, VQD-002, miltefosine, AZD5363. GDC-0068, and API-1.

Screening Compounds for Senolytic Activity

These and other compounds can be screened on the molecular level for their ability to perform in a way that indicate that they are candidate agents for use according to this invention.

For example, where the therapy includes triggering apoptosis of senescent cells by way of Bcl-2, Bcl-xL, or Bcl-w, compounds can be tested for their ability to inhibit binding between Bcl-2. Bcl-xL, or Bcl-w and their respective cognate ligand. Example 1 provides an illustration of a homogeneous assay (an assay that does not require a separation step) for purposes of determining binding to the Bcl isoforms. Compounds can be screened on the molecular level for their ability to act as agonists of MDM2, thereby promoting p53 activity and causing senolysis. Example 2 provides an illustration of an assay for this purpose.

Compounds can be screened for biological activity in an assay using senescent cells. Cultured cells are contacted with the compound, and the degree of cytotoxicity or inhibition of the cells is determined. The ability of the compound to kill or inhibit senescent cells can be compared with the effect of the compound on normal cells that are freely dividing at low density, and normal cells that are in a quiescent state at high density. Example 3 provides an illustration using the human lung fibroblast IMR90 cell line. Similar protocols are known and can be developed or optimized for testing the ability of the cells to kill or inhibit cancer cells.

Animal Models for Parkinson's Disease

Test compounds can be assessed in preclinical animal models to gain confidence in target engagement of relevant cell types and downstream readouts such as reduction of SASP or efficacy against functional endpoints in mechanistic/disease models.

Some of the data from the working examples presented below were obtained using the 3MR mouse model, which contain a transgene in which a prodrug activator (thymidine kinase) is expressed under control of the p16 promoter. This causes preferential expression of the thymidine kinase in senescent cells. Administration of the prodrug (ganciclovir) kills the senescent cells constitutively expressing the thymidine kinase. U.S. Pat. No. 9,901,080.

Exposure to the herbicide paraquat (PQ) will elicit signs of Parkinson's disease in 3MR mice and mice from other strains. The signs of the disease can be monitored for screening the effectiveness candidate senolytic agents according to this invention.

Formulation of Medicaments and their Administration

A pharmaceutical medicament according to this invention can be prepared by mixing a senolytic agent with a pharmaceutically acceptable base or carrier and as needed one or more pharmaceutically acceptable excipients. For treatment of Parkinson's disease, the medicament is formulated to deliver an effective dose to neurological tissue at or around the site of the pathophysiology of the disease, either by direct administration or by systemic administration.

This invention provides commercial products that are kits that enclose unit doses of one or more of the agents or compositions described in this disclosure. Such kits typically comprise a pharmaceutical preparation in one or more containers. The preparations may be provided as one or more unit doses (either combined or separate). The kit may contain a device such as a syringe for administration of the agent or composition in the brain of a subject in need thereof. The product may also contain or be accompanied by an informational package insert describing the use and attendant benefits of the drugs in treating the senescent cell associated Parkinson's disease, and optionally an appliance or device for delivery of the composition by the desired route of administration.

Non-limiting examples of routes and means of administration of senolytic agents include oral administration, intravenous administration, infusion (e.g. bolus injection or pump), intracranial administration, intrathecal administration, intranasal administration, intracerebroventricular administration, cisterna magna administration and intraneural administration. In some cases, administration can involve injection of a liquid formulation of the senolytic agent. In other cases, administration can involve oral delivery of a solid formulation of the senolytic agent.

Non-limiting examples of target brain regions for the treatment of Parkinson's disease include the basal ganglia, caudate nucleus, nucleus lentiformis, globus pallidus, putamen, thalamus, subthalamic nucleus, metathalamus, fornix, substantia nigra, striatum, and ventral intermediate nucleus of the thalamus. Non-limiting examples of target cell types include neurons, astrocytes, oligodendrocytes, and microglia.

Signs of neurodegenerative deficiencies and/or locomotor deficits associated with Parkinson's diseases can be assessed by histological studies, biochemical studies, and behavioral assessment (US 2012/0005765 A1). Symptoms of Parkinson's disease may include difficulty starting or finishing voluntary movements, jerky, stiff movements, muscle atrophy, shaking (tremors), and changes in heart rate, but normal reflexes, bradykinesia, and postural instability. People diagnosed with Parkinson's disease may have cognitive impairment in addition to their physical symptoms.

Formulation and administration of a senolytic agent in accordance with this invention and under supervision of a licensed health care professional may resolve, lessen, or prevent advancement of any of the aforesaid signs, symptoms, or biological markers that are manifest in Parkinson's disease in a subject, without causing intolerable adverse events.

Definitions

A "senescent cell" is generally thought to be derived from a cell type that typically replicates, but as a result of aging or other event that causes a change in cell state, can no longer replicate. It remains metabolically active and commonly adopts a senescence associated secretory phenotype (SASP) that includes chemokines, cytokines and extracellular matrix and fibrosis modifying proteins and enzymes. The nucleus of senescent cells is often characterized by senescence-associated heterochromatin foci and DNA segments with chromatin alterations reinforcing senescence. Without implying any limitation on the practice of what is claimed in this disclosure that is not explicitly stated or required, the invention is premised on the hypothesis that senescent cells cause or mediate certain conditions associated with tissue damage or aging. For the purpose of practicing this invention, senescent cells can be identified as expressing at least one marker selected from p16, senescence-associated β-galactosidase, and lipofuscin; sometimes two or more of these markers, and other markers of SASP such as but not limited to interleukin 6, and inflammatory, angiogenic and extracellular matrix modifying proteins. For the purpose of this disclosure, a senescent cell is not a cancer cell.

A "senescence associated" disease, disorder, or condition is a physiological condition that presents with one or more symptoms or signs, wherein a subject having the condition needs or would benefit from a lessening of such symptoms or signs. The condition is senescence associated if it is caused or mediated in part by senescent cells, which may be induced by multiple etiologic factors including age, DNA damage, oxidative stress, genetic defects, etc. Lists of senescence associated disorders that can potentially be treated or managed using the methods and products taught in this disclosure include those discussed in this disclosure and the previous disclosures to which this application claims priority. For the purposes of this disclosure, a senescence-associated disease suitable for treatment according to the claimed invention is not a cancer.

A compound may be referred to as "senolytic" if it eliminates senescent cells, compared with replicative cells of the same tissue type, or quiescent cells lacking SASP markers. Alternatively, or in addition, a compound or combination may effectively be used according to this invention if it decreases the release of pathological soluble factors or mediators as part of the senescence associated secretory phenotype that play a role in the initial presentation or ongoing pathology of a condition, or inhibit its resolution. In this respect, the term "senolytic" is exemplary, with the understanding that compounds that work primarily by inhibiting rather than eliminating senescent cells (senescent cell inhibitors) can be used in a similar fashion with ensuing benefits.

Certain pharmaceutical agents used for treatment of Parkinson's disease and related conditions in accordance with this invention may generally be characterized as "small molecules." These are senolytic agents having a molecular weights less than 20,000 daltons, and are often less than 10,000, 5,000, or 2,000 daltons. Small molecule inhibitors are not antibody molecules or oligonucleotides, and typically have no more than five hydrogen bond donors (the total number of nitrogen-hydrogen and oxygen-hydrogen bonds), and no more than 10 hydrogen bond acceptors (all nitrogen or oxygen atoms).

Successful "treatment" of a Parkinson's disease according to this invention may have any effect that is beneficial to the subject being treated. This includes decreasing severity, duration, or progression of a condition, or of any adverse signs or symptoms resulting therefrom. In some circumstances, senolytic agents can also be used to prevent or inhibit presentation of a condition for which a subject is susceptible because of an inherited susceptibility of because of medical history.

A "therapeutically effective amount" is an amount of a compound that (i) treats the condition, (ii) attenuates, ameliorates, or eliminates one or more symptoms of the condition, (iii) prevents or delays the onset of one or more symptoms of the condition, (iv) prevents or delays progression of the condition, or (v) at least partially reverses damage caused by the condition prior to treatment.

Unless otherwise stated or required, all the compound structures referred to in the invention include conjugate acids and bases having the same structure, crystalline and amorphous forms of those compounds, pharmaceutically acceptable salts, and dissolved and solid forms thereof, including, for example, polymorphs, solvates, hydrates, unsolvated polymorphs (including anhydrates), conformational polymorphs, and amorphous forms of the compounds, as well as mixtures of any of the aforelisted forms.

Except where otherwise stated or required, other terms used in the specification have their ordinary meaning.

INCORPORATION BY REFERENCE

For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

U.S. Pat. No. 9,849,128 (Laberge et al.) and WO 2015/116740 (Laberge et al.) are hereby incorporated herein for all purposes, including but not limited to the identification, formulation, and use of compounds capable of eliminating or reducing the activity of senescent cells and treating various neurological conditions, including Parkinson's disease.

EXAMPLES

Example 1: Measuring Bcl Inhibition

The ability of candidate compounds to inhibit Bcl-2 and Bcl-xL activity can be measured on the molecular level by direct binding. This assay uses a homogenous assay technology based on oxygen channeling that is marketed by PerkinElmer Inc., Waltham, Massachusetts: see Eglin et al., Current Chemical Genomics, 2008, 1, 2-10. The test compound is combined with the target Bcl protein and a peptide representing the corresponding cognate ligand, labeled with biotin. The mixture is then combined with streptavidin bearing luminescent donor beads and luminescent acceptor beads, which proportionally reduces luminescence if the compound has inhibited the peptide from binding to the Bcl protein.

Bcl-2, Bcl-xL and Bcl-w are available from Sigma-Aldrich Co., St. Louis, Missouri. Biotinylated BIM peptide (ligand for Bcl-2) and BAD peptide (ligand for Bcl-xL) are described in US 2016/0038503 A1. AlphaScreen® Streptavidin donor beads and Anti-6×His AlphaLISA® acceptor beads are available from PerkinElmer.

To conduct the assay, a 1:4 dilution series of the compound is prepared in DMSO, and then diluted 1:100 in assay buffer. In a 96-well PCR plate, the following are combined in order: 10 μL peptide (120 nM BIM or 60 nM BIM), 10 μL test compound, and 10 μL Bcl protein (0.8 nM Bcl-2/W or 0.4 nM Bcl-XL). The assay plate is incubated in the dark at room temperature for 24 h. The next day, donor beads and acceptor beads are combined, and 5 μL is added to each well.

After incubating in the dark for 30 minute, luminescence is measured using a plate reader, and the affinity or degree of inhibition by each test compound is determined.

Example 2: Measuring MDM2 Inhibition

MDM2 (mouse double minute 2 homolog, also known as E3 ubiquitin-protein ligase) is a negative regulator of the p53 tumor suppressor. Inhibiting MDM2 promotes p53 activity, thereby conferring senolytic activity. The ability of compounds to act as agonists for MDM2 can be measured indirectly in cells by monitoring the effect on p53.

A p53 luciferase reporter RKO stable cell line can be obtained from Signosis Inc., Santa Clara CA. In the p53 luciferase cell line, luciferase activity is specifically associated with the activity of p53. The cell line was established by transfection of a p53 luciferase reporter vector along with a G418 expression vector, followed by G418 selection.

The assay is conducted as follows. Cells from the reporter cell line are treated for 24 h with the candidate compound. Media is then removed, the cells are washed with PBS, and 20 µL of lysis buffer is added to each well. Cells are shaken for 10 s using a plate reader agitator. Luciferase buffer is prepared and added to the wells. p53 activity is then read using a Victor™ multilabel plate reader (PerkinElmer, San Jose CA).

Example 3: Measuring Senolytic Activity Using Senescent Fibroblasts

Human fibroblast IMR90 cells can be obtained from the American Type Culture Collection (ATCC®) with the designation CCL-186. The cells are maintained at <75% confluency in DMEM containing FBS and Pen/Strep in an atmosphere of 3% $O_2$, 10% $CO_2$, and ~95% humidity. The cells are divided into three groups: irradiated cells (cultured for 14 days after irradiation prior to use), proliferating normal cells (cultured at low density for one day prior to use), and quiescent cells (cultured at high density for four day prior to use).

On day 0, the irradiated cells are prepared as follows. IMR90 cells are washed, placed in T175 flasks at a density of 50,000 cells per mL, and irradiated at 10-15 Gy. Following irradiation, the cells are plated at 100 µL in 96-well plates. On days 1, 3, 6, 10, and 13, the medium in each well is aspirated and replaced with fresh medium.

On day 10, the quiescent healthy cells are prepared as follows. IMR90 cells are washed, combined with 3 mL of TrypLE trypsin-containing reagent (Thermofisher Scientific, Waltham, Massachusetts) and cultured for 5 min until the cells have rounded up and begin to detach from the plate. Cells are dispersed, counted, and prepared in medium at a concentration of 50,000 cells per mL. 100 µL of the cells is plated in each well of a 96-well plate. Medium is changed on day 13.

On day 13, the proliferating healthy cell population is prepared as follows. Healthy IMR90 cells are washed, combined with 3 mL of TrypLE and cultured for 5 minutes until the cells have rounded up and begin to detach from the plate. Cells are dispersed, counted, and prepared in medium at a concentration of 25,000 cells per mL. 100 µL of the cells is plated in each well of a 96-well plate.

On day 14, test Bcl-2 inhibitors or MDM2 inhibitors are combined with the cells as follows. A DMSO dilution series of each test compound is prepared at 200 times the final desired concentration in a 96-well PCR plate. Immediately before use, the DMSO stocks are diluted 1:200 into prewarmed complete medium. Medium is aspirated from the cells in each well, and 100 L/well of the compound containing medium is added.

Candidate senolytic agents for testing are cultured with the cells for 6 days, replacing the culture medium with fresh medium and the same compound concentration on day 17. Bcl-2 inhibitors like 001967 are cultured with the cells for 3 days. The assay system uses the properties of a thermostable luciferase to enable reaction conditions that generate a stable luminescent signal while simultaneously inhibiting endogenous ATPase released during cell lysis. At the end of the culture period, 100 µL of CellTiter-Glo® reagent (Promega Corp., Madison, Wisconsin) is added to each of the wells. The cell plates are placed for 30 seconds on an orbital shaker, and luminescence is measured.

Example 4: Senescence Markers are Expressed in Parkinsonian Midbrain Tissue

Using qPCR, we analyzed total RNA from affected substantia nigral (SN) tissues from PD patients and age-matched controls. Compared to control tissues, Parkinsonian SN tissues showed elevated expression of senescence markers, including $p16^{INK4a}$ (FIG. 1A) and several SASP factors (FIG. 1B). Among the elevated SASP factors were the pro-inflammatory cytokines interleukin (IL)-1alpha, IL-6 and IL-8 and the protease MMP-3. Elevated $p16^{INK4a}$ and MMP-3 were previously reported in cortical tissue from AD patients.

In addition to transcriptional changes in homogenized SN, indicative of increased senescence in PD tissues, we observed that astrocytes in particular showed evidence of cellular senescence in diseased tissues. Since loss of lamin B1 (LMNB1) is a senescence-associated marker detectable by immunostaining in cultured cells and intact tissue, and because senescence was demonstrated in astrocytes in aged and AD brain tissues, we assessed LMNB1 in astrocytes (GFAP– positive cells) using immunohistochemistry (IHC). Astrocytes in PD tissues showed a significant loss of LMNB1 in nuclear lamina compared to astrocytes in aged-matched control tissues (FIG. 1C). There was no significant difference between PD and aged matched control groups in the levels of LMNB1 in non-astrocytic (GFAP– negative) neighboring cells, suggesting that astrocytes are the principle cell type that undergoes senescence in PD (FIG. 1C). These findings support the idea that astrocytes, a major cell type in the brain that is capable of division, undergo senescence in vivo in humans and are more prominent in the SN of patients with PD.

Example 5: PQ Induces Cellular Senescence in Human Astrocytes

Figure 3D:
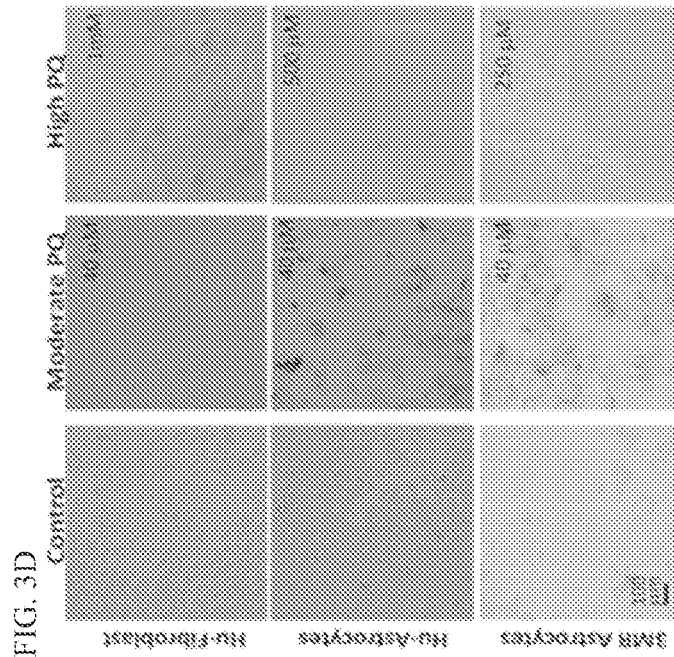
Figure 3A:
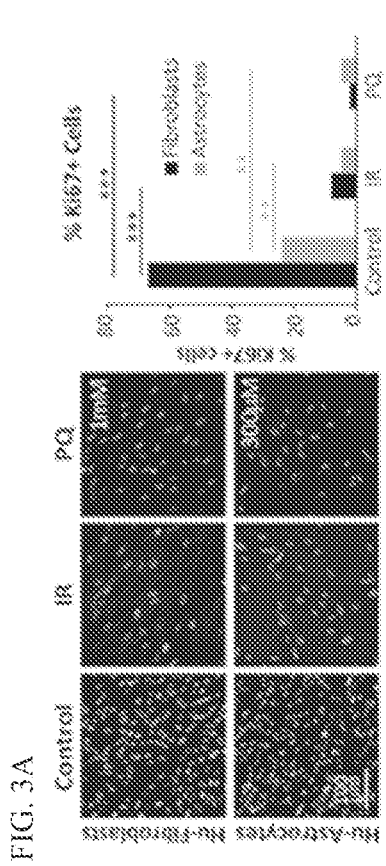
Figure 3B:
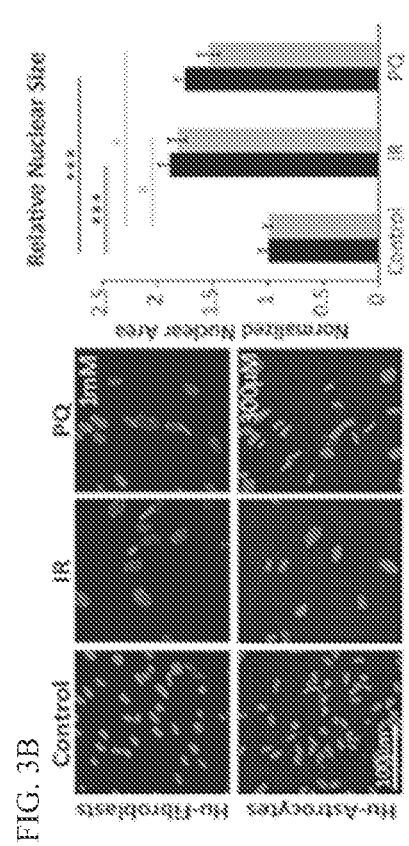

To further probe the association between astrocytic senescence and PD, we assessed the ability of astrocytes to undergo senescence in response to an environmental insult associated with PD. We exposed primary human astrocytes, differentiated from human embryonic stem cells (hESCs), to PQ (FIG. 2A to 2F). The cultured astrocytes responded to PQ with a proliferative arrest based on the decreased number of BrdU-labeled (FIG. 2A) and Ki67-positive cells (FIG. 3A). They also expressed several biomarkers associated with senescence, including senescence-associated β-galactosidase (SA-βgal) activity (FIG. 2B), increased expression of the $p16^{INK4a}$ protein (FIG. 2D) and mRNA (FIG. 2C), persistent 53BP1 foci (FIG. 2E), indicative of DNA damage signaling that activates the SASP. Consistent with induction of a SASP, PQ induced secretion of the pro-inflammatory cytokine IL-6 (FIG. 2F), a prominent component of the SASP in several cell types.

Figure 3C:
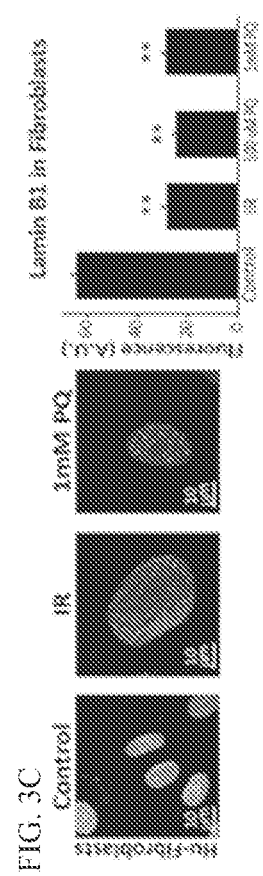

Given that genotoxic stress-induced senescence is associated with increased nuclear size and mitotic arrest, we verified that PQ caused an increase in the size of astrocyte nuclei, and decreased the number of Ki67+ cells similar to ionizing radiation (IR), an known senescence inducer. In addition, human fibroblasts cultured in PQ for 24 h displayed senescent phenotypes similar to those induced by IR, including increased nuclear size (FIG. 3B), loss of Ki67 staining (FIG. 3A) and decreased LMNB1 expression (FIG. 3C). PQ also increased SA-βgal activity in fibroblasts (FIG. 4A), validating the ability of PQ to induce senescence in both cell types. Compared to fibroblasts, human astrocytes were more sensitive to PQ-induced senescence based on SA-βgal activity and, interestingly, a concentration of PQ that induced fibroblast senescence was toxic to human astrocytes.

Example 6: The Human Astrocyte SASP Compromises the Function of Neurons and Neural Progenitor Cells Senescent cells can exert powerful paracrine effects on tissue microenvironments. For example, SASP factors include proteins that are known to stimulate inflammation, which can disrupt normal tissue structure and function. We therefore asked whether a PQ induced astrocytic SASP can drive PD-related pathologies, including dopaminergic (DAergic) neuronal cell death and loss of neural progenitor cell (NPCs) proliferation and migration.

We cultured human DAergic neurons and NPCs (both derived from hESCs) in the presence of conditioned media (CM) collected from senescent astrocytes. CM from astrocytes first induced to senesce by PQ, then washed to remove PQ, reduced DAergic neurons viability; CM from vehicle-treated astrocytes did not reduce the viability of DAergic neurons (FIG. 5A). Similarly, CM from PQ-treated astrocytes suppressed both the proliferation and migration of NPCs (FIGS. 5B-5C). Given that the DAergic neurons and NPCs were treated with CM supplemented with growth factors, depletion of trophic factors from the CM seems an unlikely explanation for our results-instead, we deduce that astrocytic senescence is likely associated with the secretion of deleterious SASP factors.

Example 7: PQ Induces Senescence In Vivo

To evaluate whether PQ induces cellular senescence in vivo and whether this induction contributes to PD-related neuropathologies, we took advantage of a mouse model we recently developed, which allows the selective killing of senescent cells. These mice, termed p16-3MR, use the promoter for the senescence marker p16$^{INK4a}$ to drive expression of a truncated herpes simplex virus thymidine kinase (HSV-TK). HSV-TK expression enables the efficient elimination of senescent cells by administering the pro-drug gancyclovir (GCV). We previously optimized GCV dosing in this mouse model such that we can eliminate >80% of senescent cells without any discernible off-target or bystander effects.

Figure 6A:
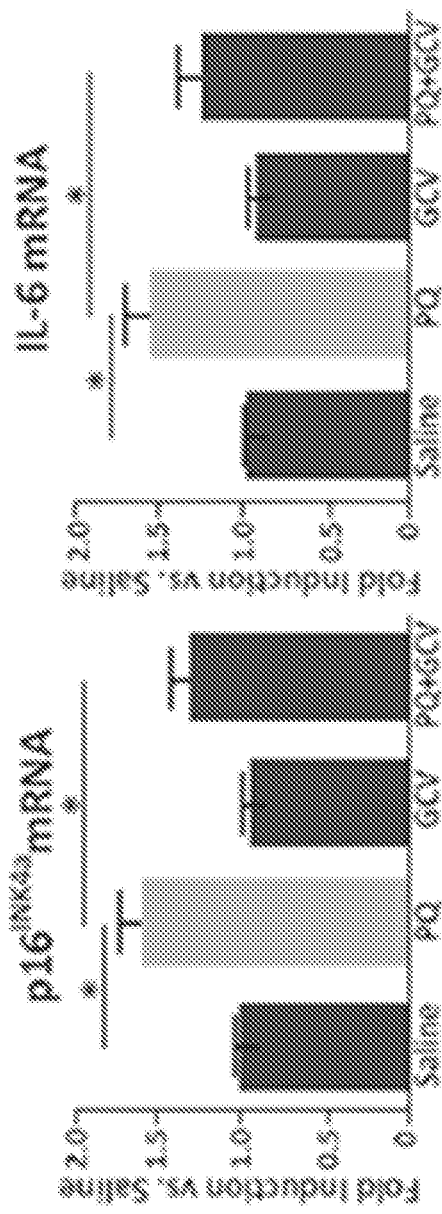
Figure 6B:
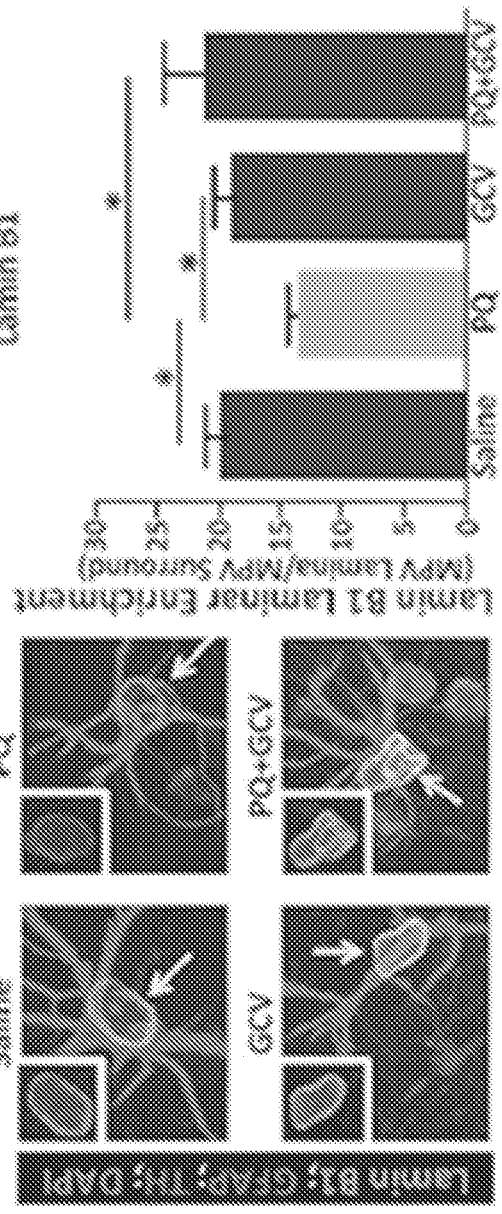
Figure 6C:
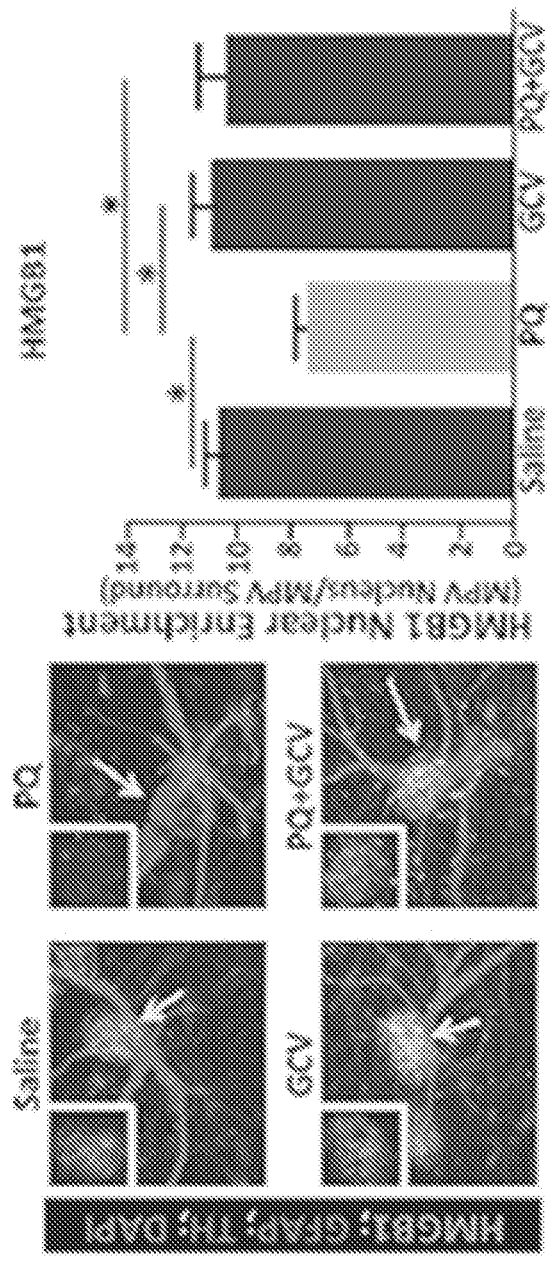

Consistent with our findings suggesting a link between senescence in the basal ganglia and PD, injection of PQ into p16-3MR mice increased mRNA levels for the senescence markers p16$^{1"K}$ and IL-6 in the mouse striatum (FIG. 6A). Corroborating PQ-induced senescence of human astrocytes, PQ treatment increased SA-βgal staining in cultured p16-3MR primary astrocytes (FIG. 6); again it was noteworthy that primary mouse astrocytes were highly sensitive to PQ-induced senescence and toxicity—and that this may be related to their relatively high SA-βgal activity even under basal conditions. In addition, IHC revealed that PQ administration caused resident SN astrocytes to adopt hallmarks of senescence, including loss of LMNB1 from the nuclear lamina (FIG. 6B) and loss of nuclear HMGB1 (FIG. 6C). While these changes indicated PQ-induced astrocytic senescence, we failed to detect reduced expression of the proliferation marker Ki67 in astrocytes in PQ treated animals (FIG. 5) most likely because basal astrocytic proliferation was very low: in saline treated mice, Ki67-positive astrocytes were extremely rare, within the range of post-mitotic neurons and far less than the Ki67-positive granule cell progenitors, which are presumed to be actively dividing in the inner layer of the dentate gyrus.

Figure 6D:
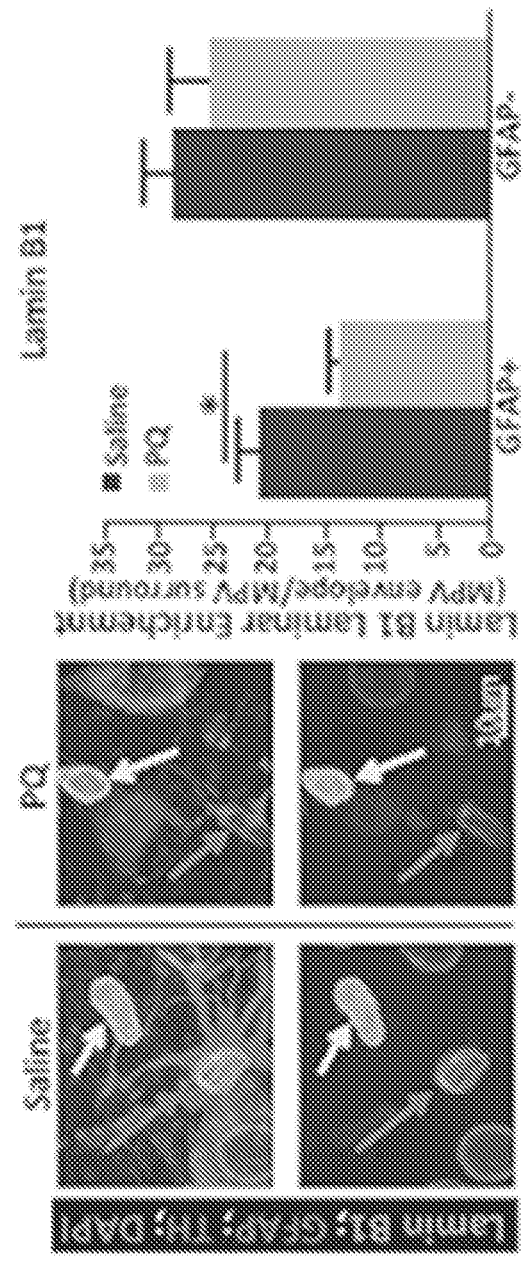

Similar to our observations in Parkinsonian SN, astrocytes may be the primary cell in the mouse SN susceptible to PQ induced senescence, given that analysis of GFAP negative neighboring cells revealed no significant difference in LMNB1 expression between PQ and saline-injected animals (FIG. 6D). All the PQ-induced senescent phenotypes in the basal ganglia (upregulation of p16$^{INK4a}$ and IL-6 mRNA and loss of astrocytic nuclear LMNB1 and HMGB1 immunostaining) were abrogated in mice in which PQ injections were immediately followed our standard GCV injection regimen (FIG. 6D and FIG. 6A).

Example 8: PQ-Induced Senescence Drives PD-Associated Neuropathologies

PD pathology is characterized by the preferential loss of DAergic neurons within the pars compacta region of the SN, which results in the diagnostic impairment of motor control. Within the pars compacta of the mouse brain (boxed region in FIG. 7A), PQ caused a significant decline in tyrosine hydroxylase (TH) positive cells, a marker for DAergic neurons; GCV treatment had no effect of TH positive cells, but PQ plus GCV treatment prevented the PQ-induced decline (FIG. 7A). Importantly, rearing behavior, a measure of motor neuron function that is more sensitive to dopamine loss compared to other tests, such as open field and pole test, was significantly blunted in mice given PQ alone, but was restored in mice treated with both PQ and GCV (FIG. 7C).

PQ also diminished neurogenesis in the brains of adult mice; this reduction was unaffected by GCV, but was partially prevented by treatment with both PQ and GCV (FIG. 7B). Thus, the elimination of senescent cells in the PQ mouse model of PD prevented three hallmarks of the disease: loss of DAergic SN neurons, impaired motor function, and depressed neurogenesis.

Example 9: Senescent Astrocytes Fail to Protect Neurons from Glutamate Excitotoxicity This experiment determined the effect of glutamate on astrocytes co-cultured with neurons.

FIG. 8 shows the results. Referring to panels (a) and (b): neurons (only DAPI-stained cells) were co-cultured with NS or SEN astrocytes (CMPTX-red+DAPI-stained cells) in neuronal media. The co-cultures were then treated for 24 h with control media without glutamate. Panel (a) shows the fluorescent images; panel (b) shows cell quantification. In panel (b), lane 1 quantifies surviving neurons (NS astrocytes+neurons co-cultures). Lane 2 quantifies surviving neurons (SEN astrocytes+neurons co-cultures). Lane 3 quantifies surviving astrocytes (NS astrocytes+neurons co-cultures). Lane 4 quantifies surviving astrocytes (SEN astrocytes+neurons co-cultures).

Referring to panels (c) and (d) of FIG. 8: neurons were co-cultured with NS or SEN astrocytes in neuronal media. In this case, the co-cultures were then treated for 24 h with media containing 10 mM glutamate. Panel (c) shows the fluorescent images; panel (d) shows cell quantification.

Conclusion: about half of the neurons cocultured with SEN (senescent) astrocytes die in the presence of 10 mM glutamate. This is instructive in the following ways:

- Parkinson's disease is caused by degeneration of dopaminergic neurons in the substantia nigra pars compacta (SnC) a nucleus in the basal ganglia responsible for voluntary movement;
- Glutamatergic stimulation in the basal ganglia has two major sources, projections from the subthalamic nucleus (STN) the only excitatory nucleus of the system, and the motor cortex. Secondary glutamatergic afferents to the SnC proceed from the amygdala;
- In Parkinson's disease, the altered neurotransmission within the basal ganglia affects the glutamatergic system, suggestions a critical involvement of glutamate-mediated excitotoxicity in the pathogenesis and progression of the disease;
- Senescent astrocytes downregulate glutamate transporters, which would explain their reduced ability to buffer extracellular glutamate, leading to mitochondrial damage and neuronal degeneration.

While this invention is often referred to in this disclosure as being applicable to Parkinson's disease, this is by way of illustration only, and does not limit the practice of the invention where not otherwise required. In particular, the invention includes treatment of other neurological conditions that are caused mediated by senescent cells, particularly senescent astrocytes, including but not limited to Amyotrophic Lateral Sclerosis (ALS). Methods of elimination of senescent cells in affected tissue include any senescent cells that may be present, unless a particular type of senescent cell is required, such as senescent neurons, astrocytes, oligodendrocytes, and microglia. The preparation of medicaments and their use for the treatment of ALS and other such neurological conditions can be derived mutatis mutandis from the illustrations provided in this disclosure for Parkinson's disease.

The several hypotheses presented in this disclosure provide a premise by way of which the reader may understand the invention. This premise is provided for the enrichment and appreciation of the reader. Practice of the invention does not require detailed understanding or application of the hypothesis. Except where stated otherwise, features of the hypothesis presented in this disclosure do not limit application or practice of the claimed invention. For example, except where the elimination of senescent cells is explicitly required, the compounds of this invention may be used for treating the conditions described regardless of their effect on senescent cells. The invention may be practiced on patients of any age having the condition indicated, unless otherwise explicitly indicated or required.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed.

The invention claimed is:

1. A method for treating a senescence-associated ocular disease or disorder in an eye of a subject in need thereof, the method comprising administering an inhibitor of a Bcl-2 anti-apoptotic protein family member, wherein the inhibitor is WEHI-539 or A-1155463, and wherein the inhibitor selectively eliminates senescent cells in the eye of the subject.

2. The method of claim 1, wherein the senescence-associated ocular disease or disorder is an age-related macular degeneration, cataracts, glaucoma, vision loss, or presbyopia.

3. The method of claim 1, wherein the inhibitor is WEHI-539.

4. The method of claim 1, wherein the inhibitor is A-1155463.

* * * * *